United States Patent [19]
Tsujimoto et al.

[11] Patent Number: 5,874,253
[45] Date of Patent: Feb. 23, 1999

[54] DNA ENCODING MEGAKARYOCYTE DIFFERENTIATION FACTOR

[75] Inventors: Masafumi Tsujimoto, Osaka; Fuyuki Iwasa, Minoo; Nobuo Tsuruoka; Hiroshi Nakazato, both of Ibaraki; Kenju Miura, Osaka; Nobuhiro Ishida, Nagaokakyo; Tatsuya Kurihara, Osaka; Kozo Yamaichi, Ibaraki; Nozomi Yamaguchi, Kyoto, all of Japan

[73] Assignee: Suntory Limited, Osaka, Japan

[21] Appl. No.: 474,661

[22] Filed: Jun. 7, 1995

Related U.S. Application Data

[62] Division of Ser. No. 91,028, Jul. 14, 1993, abandoned.

[51] Int. Cl.$^6$ .......................... C12P 21/06; C12N 15/00; C12N 5/00; C07H 21/04
[52] U.S. Cl. .................... 435/69.4; 435/69.1; 435/320.1; 435/325; 435/348; 435/410; 536/23.5; 800/2
[58] Field of Search ............................... 536/23.5; 800/2; 435/325, 348, 320.1, 410, 69.1, 69.4

[56] References Cited

FOREIGN PATENT DOCUMENTS

| 0 260 918 | 3/1988 | European Pat. Off. . |
| 0 354 989 | 2/1990 | European Pat. Off. . |
| 90/09194 | 8/1990 | WIPO . |

OTHER PUBLICATIONS

H. Mizoguchi: Tanpakushitsu Kakusan Koso, 36, 1195–1201, 1991.
T. Matsuda et al., Tanpakushitsu Koso, 36, 1184–1194, 1991.
N. Yamaguchi et al.: "Characterization of New Human Pancreatic Cancer Cell Lines Which Propagate in a Protein–free Chemically Defined Medium," *Cancer Res.*, 50, 7008–7014, 1990.
A. Dhar et al, "Platelet–Activating Factor Stimulation of Tyrosine Kinase and Its Relationship to Phospholipase C in Rabbit Platelets: Studies with Genistein and Monoclonal Antibody to Phosphotyrosine", vol. 87, 1990, p. 519–525.
Chemical Abstracts 113: 22039y, vol. 113, 1990.

*Primary Examiner*—Anthony C. Caputa
*Assistant Examiner*—Mark Navarro
*Attorney, Agent, or Firm*—Burns, Doane, Swecker & Mathis, L.L.P.

[57] ABSTRACT

A novel megakaryocyte differentiation factor, for example, consisting essentially of SEQ ID NO: 30; DNA coding for the megakaryocyte differentiation factor, an expression vector comprising the DNA, a host transformed with the expression vector, and a process for production of the megakaryocyte differentiation factor using the host. The megakaryocyte differentiation factor accelerates differentiation of megakaryocytes in the presence of IL-3, and acts as a thrombopoietin, and therefore an effective medicament to various diseases involving a decrease in platelete.

10 Claims, 13 Drawing Sheets

SEQUENCE LISTING ( 1 ) GENERAL INFORMATION:

( i i i ) NUMBER OF SEQUENCES: 34

( 2 ) INFORMATION FOR SEQ ID NO:1:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Xaa  Glu  Thr  Ile  Asn  Xaa  His  Phe  Lys
1                      5
```

( 2 ) INFORMATION FOR SEQ ID NO:2:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Xaa  Gln  Xaa  Ala  Phe  Thr  Lys
1                 5
```

( 2 ) INFORMATION FOR SEQ ID NO:3:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Val  Glu  Xaa  Val  Asp  Phe  Thr  Asn  His  Leu  Glu  Asp  Thr  Xaa  Xaa  Asn
1                 5                           10                          15
Ile  Asn  Lys
```

( 2 ) INFORMATION FOR SEQ ID NO:4:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Xaa  Tyr  Ile  Glu  Val  Thr  Glu  Glu  Gly  Thr  Glu  Ala  Xaa  Ala  Ala  Xaa
1                 5                           10                          15
Gly
```

( 2 ) INFORMATION FOR SEQ ID NO:5:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
Xaa  Tyr  Leu  Arg  Ala  Leu  Gly  Leu  Lys
1                 5
```

( 2 ) INFORMATION FOR SEQ ID NO:6:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Ala  Asp  Leu  Ser  Gly  Ile  Ala  Ser  Gly  Gly  Arg  Leu  Tyr  Ile  Ser  Arg
1                 5                           10                          15
Met  Xaa  Gly  Lys
                 20
```

( 2 ) INFORMATION FOR SEQ ID NO:7:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear (i i) MOLECULE TYPE: peptide (x i) SEQUENCE DESCRIPTION: SEQ ID NO:7:

Leu Tyr Asp Ala Lys
1               5

(2) INFORMATION FOR SEQ ID NO:8:

(i) SEQUENCE CHARACTERISTICS:
    (A) LENGTH: 5 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:8:

Asn Tyr Glu Met Lys
1               5

(2) INFORMATION FOR SEQ ID NO:9:

(i) SEQUENCE CHARACTERISTICS:
    (A) LENGTH: 10 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:9:

Ala Val Ala Met Met His Gln Xaa Arg Lys
1               5                   10

(2) INFORMATION FOR SEQ ID NO:10:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (i i) MOLECULE TYPE: DNA (genomic)

(i x) FEATURE:
    (A) NAME/KEY: misc_feature
    (B) LOCATION: 3..31
    (D) OTHER INFORMATION: /note= "Corresponding to amino acid
        sequence of SEQ ID NO: 3; N is inosine."

(x i) SEQUENCE DESCRIPTION: SEQ ID NO:10:

GTNGARNNNG TNGAYTTYAC NAAYCAY YTN GARGAYAC        38

(2) INFORMATION FOR SEQ ID NO:11:

(i) SEQUENCE CHARACTERISTICS:
    (A) LENGTH: 32 base pairs
    (B) TYPE: nucleic acid
    (C) STRANDEDNESS: single
    (D) TOPOLOGY: linear (i i) MOLECULE TYPE: DNA (genomic)

(i x) FEATURE:
    (A) NAME/KEY: misc_feature
    (B) LOCATION: 9..28
    (D) OTHER INFORMATION: /note= "Corresponding to amino acid
        sequence of SEQ ID NO: 4; N is inosine."

(x i) SEQUENCE DESCRIPTION: SEQ ID NO:11:

TACATCGANG TNACNGARGA RGGNACNGAR GC 32

( 2 ) INFORMATION FOR SEQ ID NO:12:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..37
        ( D ) OTHER INFORMATION: /note= "Oligomer attached to
            3'-RACE kit (Gibco BRL)."

( x i ) SEQUENCE DESCRIPTION: SEQ ID NO:12:

GGCCACGCGT CGACTAGTAC TTTTTTTTT TTTTTTT 37

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

ATGTTGTGGG GACTGCTATA 20

( 2 ) INFORMATION FOR SEQ ID NO:14:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

CAAGGCGAAT GACCTCTAAG TAT 23

( 2 ) INFORMATION FOR SEQ ID NO:15:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

CCCCGAAGCA ATCCCAGAGA G 21

( 2 ) INFORMATION FOR SEQ ID NO:16:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

CTCAGGCAGC AGAACGTACA T 21

(2) INFORMATION FOR SEQ ID NO:17:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

GGCGACGACT CCTGGAGCCC G 21

(2) INFORMATION FOR SEQ ID NO:18:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

GACACCAGAC CAACTGGTAA TG 22

(2) INFORMATION FOR SEQ ID NO:19:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

CATCCGGGAG ATGTACAGCC GGCCGCCAGA GGCAAT 36

(2) INFORMATION FOR SEQ ID NO:20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

GCTGTGGCCA TGATGCACCA G 21

(2) INFORMATION FOR SEQ ID NO:21:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

TACCTGCGGG CCCTGGGCCT GAAG 24

(2) INFORMATION FOR SEQ ID NO:22:

( i ) SEQUENCE CHARACTERISTICS:
    ( A ) LENGTH: 51 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:22:

CATCCGGGAG ATGTACAGCC GGCCGCCAGA GGCAATGCCA GACAGGTCAG C      51

( 2 ) INFORMATION FOR SEQ ID NO:23:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:23:

GTTTTCCCAG TCACGAC      17

( 2 ) INFORMATION FOR SEQ ID NO:24:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:24:

CAGGAAACAG CTATGAC      17

( 2 ) INFORMATION FOR SEQ ID NO:25:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:25:

AATTATGGCC CACACCAGTG      20

( 2 ) INFORMATION FOR SEQ ID NO:26:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:26:

ACTAGCCGCT ACAGTCAACA      20

( 2 ) INFORMATION FOR SEQ ID NO:27:

( i ) SEQUENCE CHARACTERISTICS:
    ( A ) LENGTH: 21 base pairs
    ( B ) TYPE: nucleic acid
    ( C ) STRANDEDNESS: single (D) TOPOLOGY: linear (ii) MOLECULE TYPE: DNA (genomic)

(xi) SEQUENCE DESCRIPTION: SEQ ID NO:27:

TTGCCACTTG CCTTTGAAGT A                                                                                                              21

(2) INFORMATION FOR SEQ ID NO:28:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

CTGATGCATC ATGGCGACTG C                                                                                                              21

(2) INFORMATION FOR SEQ ID NO:29:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

AGCATTCACC AGCACCATTA C                                                                                                              21

(2) INFORMATION FOR SEQ ID NO:30:

(i) SEQUENCE CHARACTERISTICS:
        (A) LENGTH: 1950 base pairs
        (B) TYPE: nucleic acid
        (C) STRANDEDNESS: double
        (D) TOPOLOGY: linear (ii) MOLECULE TYPE: peptide (vi) ORIGINAL SOURCE:
        (A) ORGANISM: Homo sapiens
        (B) STRAIN: A431

(ix) FEATURE:
        (A) NAME/KEY: misc_feature
        (B) LOCATION: 1
        (D) OTHER INFORMATION: /note= "DNA coding for human
        megakaryocyte differentiation factor."

(ix) FEATURE:
        (A) NAME/KEY: CDS
        (B) LOCATION: 74..1217

(xi) SEQUENCE DESCRIPTION: SEQ ID NO:30:

```
GGCACGAGAG GAACTGAAGC CCAGCTGTGA AGGCCGCAGA CTGCAGTGAG AGGAGGCTGC                 60

ACTCCATTTT GCA ATG GCC TCC CTT GCT GCA GCA AAT GCA GAG TTT TGC                   109
            Met Ala Ser Leu Ala Ala Ala Asn Ala Glu Phe Cys
             1               5                  10

TTC AAC CTG TTC AGA GAG ATG GAT GAC AAT CAA GGA AAT GGA AAT GTG                  157
Phe Asn Leu Phe Arg Glu Met Asp Asp Asn Gln Gly Asn Gly Asn Val
         15                  20                  25

TTC TTT TCC TCT CTG AGC CTC TTC GCT GCC CTG GCC CTG GTC CGC TTG                  205
Phe Phe Ser Ser Leu Ser Leu Phe Ala Ala Leu Ala Leu Val Arg Leu
     30                      35                  40

GGC GCT CAA GAT GAC TCC CTC TCT CAG ATT GAT AAG TTG CTT CAT GTT                  253
```

| | | | | | | | | | | | | | | | |
|---|---|---|---|---|---|---|---|---|---|---|---|---|---|---|---|
| Gly | Ala | Gln | Asp | Asp | Ser | Leu | Ser | Gln | Ile | Asp | Lys | Leu | Leu | His | Val |
| 45 | | | | 50 | | | | | 55 | | | | | | 60 |

| | | | | | | | | | | | | | | | | |
|---|---|---|---|---|---|---|---|---|---|---|---|---|---|---|---|---|
| AAC | ACT | GCC | TCA | GGA | TAT | GGA | AAC | TCT | TCT | AAT | AGT | CAG | TCA | GGG | CTC | 301 |
| Asn | Thr | Ala | Ser | Gly | Tyr | Gly | Asn | Ser | Ser | Asn | Ser | Gln | Ser | Gly | Leu | |
| | | | | 65 | | | | | 70 | | | | | 75 | | |

| | | | | | | | | | | | | | | | | |
|---|---|---|---|---|---|---|---|---|---|---|---|---|---|---|---|---|
| CAG | TCT | CAA | CTG | AAA | AGA | GTT | TTT | TCT | GAT | ATA | AAT | GCA | TCC | CAC | AAG | 349 |
| Gln | Ser | Gln | Leu | Lys | Arg | Val | Phe | Ser | Asp | Ile | Asn | Ala | Ser | His | Lys | |
| | | | 80 | | | | | 85 | | | | | 90 | | | |

| | | | | | | | | | | | | | | | | |
|---|---|---|---|---|---|---|---|---|---|---|---|---|---|---|---|---|
| GAT | TAT | GAT | CTC | AGC | ATT | GTG | AAT | GGG | CTT | TTT | GCT | GAA | AAA | GTG | TAT | 397 |
| Asp | Tyr | Asp | Leu | Ser | Ile | Val | Asn | Gly | Leu | Phe | Ala | Glu | Lys | Val | Tyr | |
| | | 95 | | | | | 100 | | | | | 105 | | | | |

| | | | | | | | | | | | | | | | | |
|---|---|---|---|---|---|---|---|---|---|---|---|---|---|---|---|---|
| GGC | TTT | CAT | AAG | GAC | TAC | ATT | GAG | TGT | GCC | GAA | AAA | TTA | TAC | GAT | GCC | 445 |
| Gly | Phe | His | Lys | Asp | Tyr | Ile | Glu | Cys | Ala | Glu | Lys | Leu | Tyr | Asp | Ala | |
| | 110 | | | | | 115 | | | | | 120 | | | | | |

| | | | | | | | | | | | | | | | | |
|---|---|---|---|---|---|---|---|---|---|---|---|---|---|---|---|---|
| AAA | GTG | GAG | CGA | GTT | GAC | TTT | ACG | AAT | CAT | TTA | GAA | GAC | ACT | AGA | CGT | 493 |
| Lys | Val | Glu | Arg | Val | Asp | Phe | Thr | Asn | His | Leu | Glu | Asp | Thr | Arg | Arg | |
| 125 | | | | | 130 | | | | | 135 | | | | | 140 | |

| | | | | | | | | | | | | | | | | |
|---|---|---|---|---|---|---|---|---|---|---|---|---|---|---|---|---|
| AAT | ATT | AAT | AAG | TGG | GTT | GAA | AAT | GAA | ACA | CAT | GGC | AAA | ATC | AAG | AAC | 541 |
| Asn | Ile | Asn | Lys | Trp | Val | Glu | Asn | Glu | Thr | His | Gly | Lys | Ile | Lys | Asn | |
| | | | | 145 | | | | | 150 | | | | | 155 | | |

| | | | | | | | | | | | | | | | | |
|---|---|---|---|---|---|---|---|---|---|---|---|---|---|---|---|---|
| GTG | ATT | GGT | GAA | GGT | GGC | ATA | AGC | TCA | TCT | GCT | GTA | ATG | GTG | CTG | GTG | 589 |
| Val | Ile | Gly | Glu | Gly | Gly | Ile | Ser | Ser | Ser | Ala | Val | Met | Val | Leu | Val | |
| | | | 160 | | | | | 165 | | | | | 170 | | | |

| | | | | | | | | | | | | | | | | |
|---|---|---|---|---|---|---|---|---|---|---|---|---|---|---|---|---|
| AAT | GCT | GTG | TAC | TTC | AAA | GGC | AAG | TGG | CAA | TCA | GCC | TTC | ACC | AAG | AGC | 637 |
| Asn | Ala | Val | Tyr | Phe | Lys | Gly | Lys | Trp | Gln | Ser | Ala | Phe | Thr | Lys | Ser | |
| | | 175 | | | | | 180 | | | | | 185 | | | | |

| | | | | | | | | | | | | | | | | |
|---|---|---|---|---|---|---|---|---|---|---|---|---|---|---|---|---|
| GAA | ACC | ATA | AAT | TGC | CAT | TTC | AAA | TCT | CCC | AAG | TGC | TCT | GGG | AAG | GCA | 685 |
| Glu | Thr | Ile | Asn | Cys | His | Phe | Lys | Ser | Pro | Lys | Cys | Ser | Gly | Lys | Ala | |
| | 190 | | | | | 195 | | | | | 200 | | | | | |

| | | | | | | | | | | | | | | | | |
|---|---|---|---|---|---|---|---|---|---|---|---|---|---|---|---|---|
| GTC | GCC | ATG | ATG | CAT | CAG | GAA | CGG | AAG | TTC | AAT | TTG | TCT | GTT | ATT | GAG | 733 |
| Val | Ala | Met | Met | His | Gln | Glu | Arg | Lys | Phe | Asn | Leu | Ser | Val | Ile | Glu | |
| 205 | | | | | 210 | | | | | 215 | | | | | 220 | |

| | | | | | | | | | | | | | | | | |
|---|---|---|---|---|---|---|---|---|---|---|---|---|---|---|---|---|
| GAC | CCA | TCA | ATG | AAG | ATT | CTT | GAG | CTC | AGA | TAC | AAT | GGT | GGC | ATA | AAC | 781 |
| Asp | Pro | Ser | Met | Lys | Ile | Leu | Glu | Leu | Arg | Tyr | Asn | Gly | Gly | Ile | Asn | |
| | | | | 225 | | | | | 230 | | | | | 235 | | |

| | | | | | | | | | | | | | | | | |
|---|---|---|---|---|---|---|---|---|---|---|---|---|---|---|---|---|
| ATG | TAC | GTT | CTG | CTG | CCT | GAG | AAT | GAC | CTC | TCT | GAA | ATT | GAA | AAC | AAA | 829 |
| Met | Tyr | Val | Leu | Leu | Pro | Glu | Asn | Asp | Leu | Ser | Glu | Ile | Glu | Asn | Lys | |
| | | | 240 | | | | | 245 | | | | | 250 | | | |

| | | | | | | | | | | | | | | | | |
|---|---|---|---|---|---|---|---|---|---|---|---|---|---|---|---|---|
| CTG | ACC | TTT | CAG | AAT | CTA | ATG | GAA | TGG | ACC | AAT | CCA | AGG | CGA | ATG | ACC | 877 |
| Leu | Thr | Phe | Gln | Asn | Leu | Met | Glu | Trp | Thr | Asn | Pro | Arg | Arg | Met | Thr | |
| | | 255 | | | | | 260 | | | | | 265 | | | | |

| | | | | | | | | | | | | | | | | |
|---|---|---|---|---|---|---|---|---|---|---|---|---|---|---|---|---|
| TCT | AAG | TAT | GTT | GAG | GTA | TTT | TTT | CCT | CAG | TTC | AAG | ATA | GAG | AAG | AAT | 925 |
| Ser | Lys | Tyr | Val | Glu | Val | Phe | Phe | Pro | Gln | Phe | Lys | Ile | Glu | Lys | Asn | |
| | 270 | | | | | 275 | | | | | 280 | | | | | |

| | | | | | | | | | | | | | | | | |
|---|---|---|---|---|---|---|---|---|---|---|---|---|---|---|---|---|
| TAT | GAA | ATG | AAA | CAA | TAT | TTG | AGA | GCC | CTA | GGG | CTG | AAA | GAT | ATC | TTT | 973 |
| Tyr | Glu | Met | Lys | Gln | Tyr | Leu | Arg | Ala | Leu | Gly | Leu | Lys | Asp | Ile | Phe | |
| 285 | | | | | 290 | | | | | 295 | | | | | 300 | |

| | | | | | | | | | | | | | | | | |
|---|---|---|---|---|---|---|---|---|---|---|---|---|---|---|---|---|
| GAT | GAA | TCC | AAA | GCA | GAT | CTC | TCT | GGG | ATT | GCT | TCG | GGG | GGT | CGT | CTG | 1021 |
| Asp | Glu | Ser | Lys | Ala | Asp | Leu | Ser | Gly | Ile | Ala | Ser | Gly | Gly | Arg | Leu | |
| | | | | 305 | | | | | 310 | | | | | 315 | | |

| | | | | | | | | | | | | | | | | |
|---|---|---|---|---|---|---|---|---|---|---|---|---|---|---|---|---|
| TAT | ATA | TCA | AGG | ATG | ATG | CAC | AAA | TCT | TAC | ATA | GAG | GTC | ACT | GAG | GAG | 1069 |
| Tyr | Ile | Ser | Arg | Met | Met | His | Lys | Ser | Tyr | Ile | Glu | Val | Thr | Glu | Glu | |
| | | | 320 | | | | | 325 | | | | | 330 | | | |

| | | | | | | | | | | | | | | | | |
|---|---|---|---|---|---|---|---|---|---|---|---|---|---|---|---|---|
| GGC | ACC | GAG | GCT | ACT | GCT | GCC | ACA | GGA | AGT | AAT | ATT | GTA | GAA | AAG | CAA | 1117 |
| Gly | Thr | Glu | Ala | Thr | Ala | Ala | Thr | Gly | Ser | Asn | Ile | Val | Glu | Lys | Gln | |
| | | 335 | | | | | 340 | | | | | 345 | | | | |

| | | | | | | | | | | | | | | | | |
|---|---|---|---|---|---|---|---|---|---|---|---|---|---|---|---|---|
| CTC | CCT | CAG | TCC | ACG | CTG | TTT | AGA | GCT | GAC | CAC | CCA | TTC | CTA | TTT | GTT | 1165 |
| Leu | Pro | Gln | Ser | Thr | Leu | Phe | Arg | Ala | Asp | His | Pro | Phe | Leu | Phe | Val | |
| | 350 | | | | | 355 | | | | | 360 | | | | | |

| | | | | | | | | | | | | | | | | |
|---|---|---|---|---|---|---|---|---|---|---|---|---|---|---|---|---|
| ATC | AGG | AAG | GAT | GAC | ATC | ATC | TTA | TTC | AGT | GGC | AAA | GTT | TCT | TGC | CCT | 1213 |

| Ile | Arg | Lys | Asp | Asp | Ile | Ile | Leu | Phe | Ser | Gly | Lys | Val | Ser | Cys | Pro |
| 365 | | | | | 370 | | | | | 375 | | | | | 380 |

```
TGA A      AATCCAATTG  GTTTCTGTTA  TAGCAGTCCC  CACAACATCA  AAGAACCACC          1267
*

ACAAGTCAAT  AGATTTGAGT  TTAATTGGAA  AAATGTGGTG  TTTCCTTTGA  GTTTATTTCT          1327

TCCTAACATT  GGTCAGCAGA  TGACACTGGT  GACTTGACCC  TTCCTAGACA  CCTGGTTGAT          1387

TGTCCTGATC  CCTGCTCTTA  GCATTCTACC  ACCATGTGTC  TCACCCATTT  CTAATTTCAT          1447

TGTCTTTCTT  CCCACGCTCA  TTTCTATCAT  TCTCCCCCAT  GACCCGTCTG  GAAATTATGG          1507

AGAGTGCTCA  ACTGGTAAGG  AGAACGTAGA  AGTAGCCCTA  GGGATCCTTT  TTGAAACTCT          1567

ACAGTTATCG  CAGATATTCT  AGCTTCATTG  TAAGCAATCT  AGGAAATAAG  CCCTGCTGCT          1627

TTCTAGAAAT  AAGTGTGAAG  GATAAATTTT  CTTTGTTGAC  CTATGAAGAT  TTTAGAGTTT          1687

ACCTTCATAT  GTTTGATTTT  AAATCAGTGT  ATAATCTAGA  TGGTAAAAAA  TGTGAAATTG          1747

GGATTAGGGA  CCAACCAAAA  TATTTCATTA  ATGCTTTCAA  TTGACAAATT  TTGGTCTTTC          1807

TTTGATAAGA  CAATATGTAC  ATAGTTTTT   CAAATATTAA  AGATCTTTTA  ACTGTTGGCA          1867

GTTGTTATCT  ACAGAATCAT  ATCTCATATG  CTGTGTAGTT  TATAAGTTTT  TTCTCTATTT          1927

ATCAGAATAA  AGAAATACAA  CAT                                                    1950
```

( 2 ) INFORMATION FOR SEQ ID NO:31:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Homo sapiens ( i x ) FEATURE:
        ( A ) NAME/KEY: misc_feature
        ( B ) LOCATION: 1
        ( D ) OTHER INFORMATION: /note= "5'-non-translation region."

( x i ) SEQUENCE DESCRIPTION: SEQ ID NO:31:

```
AACTGAAGCC  CAGCTGTGAA                                                         20
```

( 2 ) INFORMATION FOR SEQ ID NO:32:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:32:

```
CTCGAATTCG  CGATGGCCTC  CCTTGCTGCA  GCAAATG                                    37
```

( 2 ) INFORMATION FOR SEQ ID NO:33:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:33:

GGGAATTCGC GGCCGCGTGG TGGTTCTTTG ATGTTGTGGG GACTGCTAT    49

(2) INFORMATION FOR SEQ ID NO:34:

(i) SEQUENCE CHARACTERISTICS:
        (A) LENGTH: 380 amino acids
        (B) TYPE: amino acid
        (D) TOPOLOGY: linear (ii) MOLECULE TYPE: protein (xi) SEQUENCE DESCRIPTION: SEQ ID NO:34:

```
Met Ala Ser Leu Ala Ala Ala Asn Ala Glu Phe Cys Phe Asn Leu Phe
 1               5                  10                  15
Arg Glu Met Asp Asp Asn Gln Gly Asn Gly Asn Val Phe Phe Ser Ser
            20                  25                  30
Leu Ser Leu Phe Ala Ala Leu Ala Leu Val Arg Leu Gly Ala Gln Asp
        35                  40                  45
Asp Ser Leu Ser Gln Ile Asp Lys Leu Leu His Val Asn Thr Ala Ser
    50                  55                  60
Gly Tyr Gly Asn Ser Ser Asn Ser Gln Ser Gly Leu Gln Ser Gln Leu
65                  70                  75                  80
Lys Arg Val Phe Ser Asp Ile Asn Ala Ser His Lys Asp Tyr Asp Leu
                85                  90                  95
Ser Ile Val Asn Gly Leu Phe Ala Glu Lys Val Tyr Gly Phe His Lys
            100                 105                 110
Asp Tyr Ile Glu Cys Ala Glu Lys Leu Tyr Asp Ala Lys Val Glu Arg
        115                 120                 125
Val Asp Phe Thr Asn His Leu Glu Asp Thr Arg Arg Asn Ile Asn Lys
    130                 135                 140
Trp Val Glu Asn Glu Thr His Gly Lys Ile Lys Asn Val Ile Gly Glu
145                 150                 155                 160
Gly Gly Ile Ser Ser Ser Ala Val Met Val Leu Val Asn Ala Val Tyr
                165                 170                 175
Phe Lys Gly Lys Trp Gln Ser Ala Phe Thr Lys Ser Glu Thr Ile Asn
            180                 185                 190
Cys His Phe Lys Ser Pro Lys Cys Ser Gly Lys Ala Val Ala Met Met
        195                 200                 205
His Gln Glu Arg Lys Phe Asn Leu Ser Val Ile Glu Asp Pro Ser Met
    210                 215                 220
Lys Ile Leu Glu Leu Arg Tyr Asn Gly Gly Ile Asn Met Tyr Val Leu
225                 230                 235                 240
Leu Pro Glu Asn Asp Leu Ser Glu Ile Glu Asn Lys Leu Thr Phe Gln
                245                 250                 255
Asn Leu Met Glu Trp Thr Asn Pro Arg Arg Met Thr Ser Lys Tyr Val
            260                 265                 270
Glu Val Phe Phe Pro Gln Phe Lys Ile Glu Lys Asn Tyr Glu Met Lys
        275                 280                 285
Gln Tyr Leu Arg Ala Leu Gly Leu Lys Asp Ile Phe Asp Glu Ser Lys
    290                 295                 300
Ala Asp Leu Ser Gly Ile Ala Ser Gly Gly Arg Leu Tyr Ile Ser Arg
305                 310                 315                 320
Met Met His Lys Ser Tyr Ile Glu Val Thr Glu Glu Gly Thr Glu Ala
                325                 330                 335
Thr Ala Ala Thr Gly Ser Asn Ile Val Glu Lys Gln Leu Pro Gln Ser
            340                 345                 350
```

```
Thr Leu Phe Arg Ala Asp His Pro Phe Leu Phe Val Ile Arg Lys Asp
    355                 360                 365

Asp Ile Ile Leu Phe Ser Gly Lys Val Ser Cys Pro
    370             375             380
```

DNA ENCODING MEGAKARYOCYTE DIFFERENTIATION FACTOR

This application is a divisional, of application Ser. No. 08/091,028, filed Jul. 14, 1993 now abandonded.

BACKGROUND OF THE INVENTION

1. Field of the Invention

The present invention relates to a megakaryocyte differentiation factor, gene coding for the factor and a process for production thereof. The megakaryocyte differentiation factor is useful as a hemopoietic stimulating factor for megakaryocyte-platelet lineage.

2. Description of Related Art

It is well known that various hemopoietic factors inducing the growth and differentiation of blood cells are involved in a process from hemopoietic stem cells to mature blood cells.

Although the life time of platelet is as short as 9 to 10 days, concentration of platelets in the blood is maintained rather constant during the stationary state. Moreover, when the number of platelets is artificially reduced by one of various available method in an experimental animals, the number of the platelets recovers in the blood in a few days. From these facts, it is supposed that factors which stimulate formation of platelets are present, and so far a great effort has been made to identifycation of the factors.

It is considered that at least two regulatory factors are involved in the megakaryocyte-platelet hemopoietic lineage. The first factor by itself stimulates formation of megakaryocyte colonies and is called a megakaryocyte colony stimulating factor. The second factor by itself does not have an activity to stimulate formation of megakaryocyte colonies, but in combination with the first factor, increases the number of megakaryocyte colonies and stimulates the differentiation thereof, and is called a megakaryocyte potentiator.

The former includes interleukin 3, and granulocyte/macrophage colony stimulating factor, and the latter includes erythropoietin, macrophage colony stimulating factor, interleukin 6, 7 and 11, LIF, and the like. Some of these factors actually exhibit in vivo effect of increasing the number of platelets or shortening the time required to recover the number of platelets (Hideaki Mizoguchi: Tanpakushitsu Kakusan Koso 36, 1195, 1991 in Japanese).

However, most of these factors exhibit a diversity of biological activities other than participation in differentiation of blood cells in various hemopoietic lineages including differentiation in megakaryocyte-platelet lineages. For example, although IL-6 and IL-11 actually exhibit in vivo thrombopoietic action, they stimulate production of acute phase protein, and in severe cases, cause cachexia. Moreover, IL-6 is accompanied with various clinical problems; for example, it is possible for IL-6 to stimulate the growth of mesangium cells in the kidney resulting in renal failure (Tadashi Matsuda et al., Tanpakushitsu Kakusan Koso, 36, 1184, 1991 in Japanese). In addition, since IL-6 does not exhibit a high blood level during a thrombcytopenic phase, it is not considered as a physiological factor.

Platelets play an important role in a hemostatic mechanism. Diseases involving decrease of platelets (Fanconi's syndrome, megakaryocytic thrombocytopenia, aplastic anemia, and the like) are clinically dangerous, and in particular hemorrhaging cannot be controlled. Therefore, it is considered that isolation and identification of a factor which stimulates production of platelets is useful to prevent the above-mentioned danger.

Currently, bone marrow transplantation is becoming a powerful therapeutic means for treating leukenia etc., and the ratio of successful cases is increasing through the use of cytokines such as erythropoietin (EPO), granulocyte colony stimulating factor (G-CSF) etc. At present a problem in the bone marrow transplantation is a decrease in the number of platelets, and if a thrombopoietic factor is available, it is expected that the ratio of successful cases will increase and a period of hospitalization will be shortened. Not only hemopoietic diseases but also thrombocytopenia in chemotherapy and radio isotopic therapy of cancers may be controlled by thrombopoietin.

The present inventors, considering the various above-mentioned difficulties with known factors, carried out various research to find a factor which stimulates production of platelets and is effective for treatment of patients having thrombocytopenia or insufficient platelet function, and as a result, the present inventors found a novel factor which stimulates differentiation of megakaryocytes, cloned a gene coding for said factor, constructed an expression vector, and succeeded in expressing the gene to produce said factor.

SUMMARY OF THE INVENTION

Accordingly, the present invention provides a megakaryocyte differentiation factor having the following properties;

(1) stimulating differentiation of megakaryocytes;

(2) exhibiting a molecular weight of 55 to 57 kD as determined by gel filtration and SDS-polyacrylamide gel electrophoresis (SDS-PAGE), and having no intermolecular disulfide linkage;

(3) exhibiting an isoelectric point of 6.5±0.5; and (4) having at least one of the amino acid sequences shown in SEQ ID NO: 1 to 9 in the Sequence Listing.

The present invention also provides a gene coding for the megakaryocyte differentiation factor.

The present invention further provides an expression vector comprising the gene coding for the megakaryocyte differentiation factor.

The present invention moreover provides a host transformed with the expression vector.

The present invention still further provides a process for production of the megakaryocyte differentiation factor using said host.

DETAILED DESCRIPTION

Figure 1:
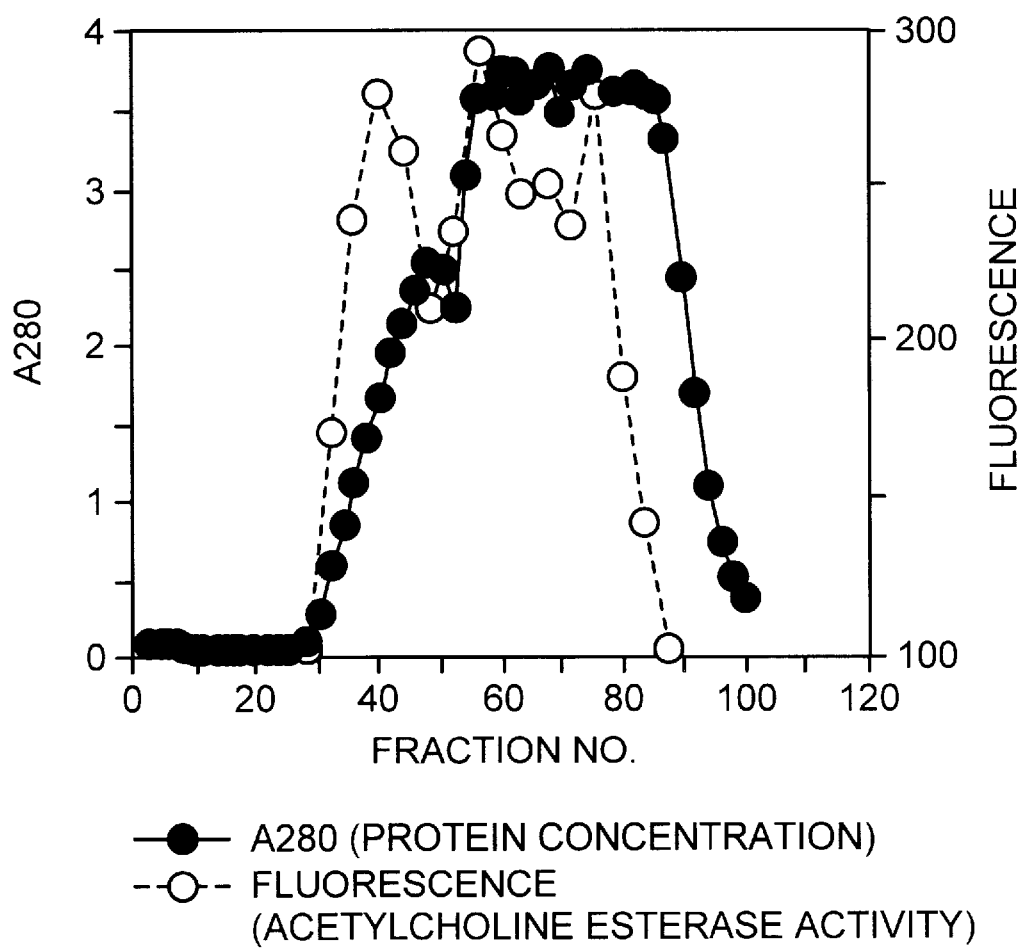
FIG. 1 shows an elution profile of protein (A280 —●—) and a megakaryocyte differentiation factor (acetylcholine esterase activity —○—) from a Q-Sepharose column, wherein the elution was carried out by NaCl concentration gradient (0 to 1.0M) to obtain fractions 1 to 120.

As starting materials for isolating the present megakaryocyte differentiation factor, human cells, such as human cancer cells, preferably human epidermoid carcinoma cells A431, particularly preferably human epidermoid carcinoma A431 grown in a protein-free medium can be mentioned.

In addition to the above-defined megakaryocyte differentiation factor, the present invention relates to megakaryocyte differentiation factors obtainable from transformants such as cells or animals constructed by gene technology and having the same amino acid sequence as the above-defined megakaryocyte differentiation factor, an amino acid sequence wherein a portion of the above-defined megakaryocyte differentiation factor is deleted, an amino acid sequence wherein a portion of the above-defined megakaryocyte differentiation factor is replaced with other amino acid or amino acid sequence, or an amino acid sequence wherein one or more than one amino acid sequence is added to the above-defined megakaryocyte differentiation factor, or having an amino acid sequence including a combination of said modifications.

Moreover, the present invention relates to megakaryocyte differentiation factor having the amino acid sequence shown in SEQ ID NO: 30, an amino acid sequence wherein a portion of the amino acid sequence shown in SEQ ID NO: 30 is deleted, an amino acid sequence wherein a portion of the amino acid sequence shown in SEQ ID NO: 30 is replaced with another amino acid or amino acid sequence, or an amino acid sequence wherein one or more than one amino acid sequence is added to the amino acid sequence shown in SEQ ID NO: 30, or having an amino acid sequence including a combination of said modifications.

The present invention also relates to genes coding for the above-mentioned megakaryocyte differentiation factors. The present invention further relates a process for production of the megakaryocyte differentiation factors using the gene by means of gene recombination technology. The gene recombination technology follows conventional procedures by using a synthetic or natural polynucleotide coding for the amino acid sequence of the native megakaryocyte differentiation factor, an amino acid sequence wherein a portion of the native amino acid sequence is deleted, an amino acid sequence wherein a portion of the native amino acid sequence is replaced with other amino acid or amino acid sequence, or an amino acid sequence wherein one or more than one amino acid is added to the native amino acid sequence, or coding for an amino acid sequence including a combination of said modifications, but not limited to the above.

The above-mentioned various modifications can be carried out by a conventional technique such as site-specific mutagensis.

The number of amino acids involved in the modification, such as addition, deletion or replacement, is not limited. For addition, the number of amino acid depends on the number of amino acids, for example, that of the functional peptide used in a hybrid protein with the megakaryocyte differentiation factor of the present invention or that of a signal peptide added to the present factor, namely depends on purpose of the modification. For deletion, the number of amino acids may be designed or determined so as to maintain megakaryocyte differentiation activity and it is, for example, 1 to 30, preferably 1 to 20 or it can be that of region other than the active region of the present factor. For replacement, the number of amino acids also may be designed or determined so as to maintain megakaryocyte differentiation activity and it is, for example, 1 to 10, preferably, 1 to 5.

An addition or improvement of a signal sequence, choice of host-vector system, and improvement of expression regulatory region may provide efficient expression. In addition, a host may be chosen to provide a glycosylated product. Moreover, a polynucleotide coding for at least one of the amino acid sequences shown in SEQ ID NO: 1 to 9 may be used as a DNA probe for cloning a gene.

The present invention further provides a pharmaceutical composition comprising a megakaryocyte differentiation factor as an effective ingredient. The pharmaceutical composition is preferably used as a medicament for thrombocytopenia.

In addition, the present megakaryocyte differentiation factors can be used to obtain specific antibodies according to a known procedure.

Now, the present invention is explained in more detail.

(1) Starting material

As a starting material for obtaining a novel protein of the present invention, a culture supernatant of cells derived from human epidermoid carcinoma cell A431 (ATCC CRL 1555), rendered to be capable of growing in a protein-free medium according to Yamaguchi et al. method (Yamaguchi N. et al., Cancer Res. 50, 7008, 1991), is mentioned. This cell line was designated as Human epidermoid carcinoma SBM 330, and deposited as FERM BP-3911 with the Fermentation Research Institute Agency of Industrial Science and Technology, 1–3, Higashi 1-chome, Tsukuba-shi Ibraki-ken (307) Japan, on Jul. 1, 1992.

(2) Assay method for megakaryocyte differentiation factor

To assay a megakaryocyte differentiation factor, megakaryocyte-series cell lines (for example, CMK cells or cells derived therefrom), or mouse bone marrow cells may be used. For example, activity of acetylcholine esterase which is known to be specifically detected in murine megakaryocytes is carried out using mouse bone marrow cells according to the Ishibashi et al. method (Ishibashi, T. et al., Proc. Natl. Acad. Sci. USA 86, 5953, 1989). In addition, histochemical detection of megakaryocytes is carried out by subjecting cultured bone marrow cells to acetylcholine esterase staining and May-Gruenwald-Giemsa's staining and the observing the shape of the stained cells.

(3) Purification of megakaryocyte differentiation factor

The megakaryocyte differentiation factor can be purified, for example, starting from a culture supernatant of A431 cells cultured in a protein-free medium, concentration by ultrafiltration, and column chromatography using, for example, Matrex Blue A (Amicon), Q-Sepharose (Pharmacia), phenyl-Sepharose (Pharmacia), S-Sepharose (Pharmacia) and Hiload 26/60 Superdex 75 (Pharmacia) alone or in combination. Protein is monitored by measuring A280 nm.

(4) Determination of partial amino acid sequence of megakaryocyte differentiation factor To determine an amino acid sequence, the megakaryocyte differentiation factor purified in the section (3) is digested into fragments with a protease such as Achromobacter Protease I (API) at 37° C. for 2 hours. The resulting peptide fragments are separated and recovered by reverse phase HPLC (acetonitrile gradient in 0.1% trifluoroacetic acid) using YMC-Pack AM-303 column. The peptide fragments thus obtained are subjected to a sequencer such as a gas-phase sequencer obtained from, for example, Applied Biosystem. A definite purification process and detailed properties of the megakaryocyte differentiation factor are described in Example 1.

The present invention also provides gene coding for megakaryocyte differentiation factor. The gene may be cDNA prepared from mRNA, genomic DNA, and synthetic DNA. For example, cDNA can be cloned by a polymerase chain reaction (PCR) using DNA (nucleotide) primers designed on the basis of partial amino acid sequences as shown in Example 1 of a megakaryocyte differentiation factor purified from the above-mentioned human cells, such as human epidermoid carcinoma cells, for example A431 cells. The cloning is described in detail in Examples 1 and 2.

The gene of the present invention further includes DNAs coding for protein or glycoprotein having megakaryocyte differentiation activity and hybridizing with the nucleotide sequence of SEQ ID NO: 30. Nucleotide sequence of DNA cloned in Example 2 and an amino acid sequence predicted from the nucleotide sequence are shown in SEQ ID NO: 30.

Thus once an amino acid sequence is determined, various mutated megakaryocyte differentiation factors, such as a polypeptide, wherein one or more than one amino acid is added to the native amino acid sequence or the amino acid sequence shown in SEQ ID NO: 30 and maintaining megakaryocyte differentiation factor activity, a polypeptide wherein one or more than one amino acid is deleted from the native amino acid sequence or the amino acid sequence shown in SEQ ID NO: 30 and maintaining megakaryocyte differentiation factor activity, a polypeptide wherein one ore more than one amino acid is replaced with one or more than one other amino acid, in the native amino acid sequence or the amino acid sequence shown in SEQ ID NO: 30, and maintaining megakaryocyte differentiation factor activity, or a polypeptide including a combination of the above-mentioned modifications such as addition, deletion and/or replacement of amino acids maintaining megakaryocyte differentiation factor activity can be designed and produced.

According to the present invention, although the nucleotide sequence shown in SEQ ID NO: 30 is disclosed, gene coding for the present megakaryocyte differentiation factor is not limited thereto. Once an amino acid sequence of the present native megakaryocyte differentiation factor or an amino acid sequence of a mutated megakaryocyte differentiation factor is determined, according to the degeneracy of genetic code, various nucleotide sequences coding for the same amino acid sequence can be designed and prepared. In this case, codons used with a high frequency in a chosen host are preferably used.

A gene coding for the present megakaryocyte differentiation factor can be obtained as cDNA according to Example 2, but the gene is not limited to cDNA. Namely, once a nucleotide sequence coding for an amino acid sequence of native megakaryocyte differentiation factor is determined, a gene coding for the native megakaryocyte differentiation factor can be cloned as a cDNA according to a strategy different from the strategy definitely described herein, and moreover a desired gene can be cloned from the genome of a cell producing the megakaryocyte differentiation factor.

Where a desired gene is cloned from the genome, various primer nucleotides or probe nucleotides used in Example 2 can be used as probes for screening genomic DNA fragments. Moreover, other probes designed on the basis of the nucleotide sequence described in SEQ ID NO: 30 can be used. General procedures for cloning a desired DNA from a genome are well known in the art (see Current Protocols In Molecular Biology, John Wiley & Sons, Chapters 5 and 6).

Gene coding for the native megakaryocyte differentiation factor of the present invention can also be prepared by chemical synthesis. It is easy in the art to chemically synthesize DNA using an automated DNA synthesizer, for example, Applied Biosystems 396 DNA/RNA synthesizer. Accordingly a person with ordinary skill in the art can easily synthesize DNA having the nucleotide sequence shown in SEQ ID NO: 30.

A gene coding for the present native megakaryocyte differentiation factor using codons different from native codons, and a gene coding for a mutated megacaryocyte differentiation factor can be prepared by chemical synthesis as described above. Alternatively they can be obtained by site-specific mutagenesis using as a templete a DNA or RNA having a nucleotide sequence shown in SEQ ID NO: 30 together with mutagenic primers (for example, see, Current Protocols In Molecular Biology, John Wiley & Sons, Chapter 8).

Once a gene coding for the present megakaryocyte differentiation factor is obtained, the gene can be used to produce a recombinant megakaryocyte differentiation factor according to a conventional gene recombination technology. Namely, a DNA coding for the present megakaryocyte differentiation factor is inserted into an appropriate expression vector, the vector is introduced to appropriate host cells, the transformed host cells are cultured, and the target megakaryocyte differentiation factor is recovered from the culture (cells or medium). The present megakaryocyte differentiation factor can be biochemically or chemically modified, for example, N-terminal acylated.

In addition, on the basis of the nucleotide sequence shown in SEQ ID NO: 30, a protein data base was searched with fasta Program (GCG package). As a result, the megakaryocyte differentiation factor belongs to the super family of serine protease inhibitor. On the other hand, in human leucocyte elastase inhibitor, chicken ovalbumin Y gene product, human plasminagen activator inhibitor 2 and human squamous cell carcinoma antigen, which are similar to the present megakaryocyte differentiation factor in their expected steric structure, and distribution of hydrophobic and hydrophilic amino acids, the N-terminal portion is not cleaved and forms a signal peptide. Accordingly, there is a possibility that in the present megakaryocyte differentiation factor, the N-terminal portion may function as a signal peptide and the megakaryocyte differentiation factor may be secreted without cleavage of the signal peptide. Further, the present megakaryocyte differentiation factor may be modified so that the first methionine is deleted and the second alanine is acetylated.

As hosts, both the prokaryote and enkaryote can be used. As prokaryote, bacteria such as *Escherichia coli* the genus Bacillus, for example, *B. subtilis* and the like can be used. As eukaryote, yeast such as the genus Saccharomyces, for example, *S. serevisiae*, insect cells such as *Spodoptera frugiperda* cells, *Cabbage looper* cells, *Bombyx mori* cells, animal cells such as human cells, monkey cells, mouse cells and the like can be used. Moreover, insects per se, such as *Bombyx mori* may be used.

As expression vectors, plasmid, phage, phagemid, virus such as bacuro virus, vaccinia virus or the like can be used. A promoter in an expression vector is selected depending on host used. For example, lac promoter, trp promoter and the like can be used as bacterial promoters, and adhl promoter, pqk promoter and the like can be used as yeast promoters. On the other hand, baculovirus polyhedrin promoter can be used as insect promoter, and Simian virus 40 early or late promoter can be used for animal cells.

Transformation of a host with an expression vector can be carried out according to conventional procedures well known in the art, and these procedures are described in, for example, Current Protocols in Molecular Biology, John Wiley & Sons. Culturing of a transformant also can be carried out according to a conventional procedure.

Purification of a megakaryocyte differentiation factor from a culture or an insect body can be carried out according to conventional procedures used for isolation and purification of a protein, for example, ultrafiltration, various types of column chromatography such as Q-Sepharose column chromatography and the like.

EXAMPLES

Next, the present invention is further explained by Examples.

Example 1. Purification of megakaryocyte differentiation factor (1) Culturing of A431 cells Frozen SBM 330 cells conditioned in a protein-free medium from A431 cells were thawed, and cultured in a primary medium (Ham's F12 medium containing 10% fetal bovine serum). Namely, the cells were plated in 10 T flasks having a culture area of 150 $cm^2$, and cultured to confluence at 37° C. in the presence of 5% $CO_2$. Next, the cells were peeled off with a 0.25% trypsin solution (Chiba Kessei) and subcultured in 10 roller bottles having a culture area of 850 $cm^2$ at 37° C. and 0.5 rpm for about 3 days to recover $1.8 \times 10^9$ cells. The cultured cells were attached to a ceramic core (S-451) of an Opti-cell incubator (Charles River Inc. Wilmington, Mass.) and perfusion culturing was started using 10 L of a primary medium.

The perfusion culture was carried out at 37° C. with supplying oxygen at 150 mmHg. The primary medium was replaced with a protein-free medium as follow. Namely, after culturing for about 7 days in a primary medium, a protein-free medium was supplied to the culture at a rate of 20 L/day, and simultaneously the culture supernatant was recovered from the culture at the same rate. As a result, the primary medium containing serum was substantially completely replaced with the protein-free medium by supplying about 100 L of the protein-free medium. Thereafter, cell culture supernatant was continuously recovered to obtain 1000 L of cell culture supernatant. A part (about 300 L) of the cell culture supernatant thus obtained was concentrated to 2 L using an ultrafiltration membrane (Milipore, Bedford, Mass.; MW 10,000 cut) and the concentrate was dialyzed against 20 mM Tris/HCl buffer (pH 7.4).

(2) Assay of megakaryocyte differentiation factor using mouse bone marrow cells

Myeloid cells were pushed out of the femur of female $BDF_1$ mouse and suspended in an α-MEM medium (Flow Laboratories, Inc. McLean, Va., USA). Percoll layers having different densities (Pharmacia LKB Biotechnology, Tokyo) were overlaid, and the bone marrow cell suspension was put thereon, followed by centrifugation at 400×g for 20 minutes. Mononuclear cells collected at the interface of a layer having a density of 1.07 g/ml and a layer having a density of 1.08 g/ml were recovered and washed once with α-MEM containing 10% FBS, and resuspended in the same medium containing 0.5 mM diisopropylfluorophosphate. The suspension was then put into a plastic cell culture dish (Corning, N.Y., USA) and cultured at 37° C. in 5% carbon dioxide and 95% air for 2 hours. During the culturing, at one hour from the start of culturing, the cell culture dish was replaced with a new one. After the culturing, cells were washed with 10% FBS/α-MEM three times.

The non-adherent bone marrow mononuclear cells thus obtained were suspended in 10% FBS/1% BSA/0.1 mM 2-mercaptoethanol/α-MEM, and plated in a 96-well microplate (Corning) in an amount of $5 \times 10^4$ cell/well. If necessary, to a test sample were added 25 U/ml mouse recombinant IL-3 (Genzyme Corporation, Cambridge, Mass., USA) and 1 to 2 μg/ml anti-IL-6 antibody (Boehringer Mannheim, Mannheim, FRG). Where anti-IL-6 antibody was added, the test sample and the antibody were preincubated at 37° C. for an hour prior to seeding the cells.

The culturing was carried out at 37° C. in 5% $CO_2$-5% $O_2$-90% $N_2$ for 4 to 5 days. After culturing cells in each well of the microplate they were washed twice with PBS, and lysed with 180 μl of 0.2% (w/v) Triton X-100, 1 mM EDTA, 0.12M NaCl, 50 mM HEPES (pH 7.5), and 20 μl of a substrate, 5.6 mM acetylthiocholine iodide, was added thereon. After culturing with shaking at a room temperature for an hour, 20 μl of the solution was transferred to a microplate for fluorescent assay (Dynatech Micro FLUOR "B" Plate).

To the microplate were added 20 μl of 0.4 mM 7-diethylamino-3-(4'-maleimidylphenyl)-4-methylcoumarine in acetonitrile and 160 μl of 0.2% (w/v) Triton X-100, 1 mM EDTA, 50 mM sodium acetate (pH 5.0), and fluorescent emission was measured by a fluorometer (excitation 365 nm, emission 450 nm).

For acetylcholine esterase staining, the cells were centrifuged by a Cytospin to adhere the cells onto a slide glass, and fixed with 5% glutaraldehyde, 10 mM phosphate buffer (pH 6.7) for 15 minutes, and as a substrate acetylthiocholine was used according to Mizoguchi's method (Method for Culturing Hemopoietic Stem Cells, Chugai Igaku, 1986, ed. Y. Miura, pp82–88). Namely, after fixing the cells, the slide glass was washed with 0.1M phosphate buffer (pH 6.0), and to each slide glass was layered a mixture of 1.5 ml of 0.67 mg/ml acetylthiocholine iodide, 0.1M phosphate buffer (pH 6.0), 0.2 ml of 30 mM $CuSO_4$, 0.2 ml of 5 mM potassium ferricyanide and 0.1 ml of 0.1M sodium citrate. The slide glass was incubated at a room temperature for 4 hours, and washed with water. May-Gruenwald-Giemsa's staining is well known in hematology and was carried out using reagents available from E. Merck (Darmstadt, FRG) wherein May-Gruenwald's staining was carried out for 4 minutes and Giemsa's staining was carried out for 10 minutes.

(3) Purification of megakaryocyte differentiation factor

A culture supernatant concentrate of A431 cells was dialyzed and centrifuged to obtain a supernatant which was then applied to a Matrex Blue A Column equilibrated with 20 mM Tris/HCl buffer (pH 7.4), and after washing the column with the same buffer, a bound fraction was eluted with the same buffer containing 2M NaCl. Megakaryocyte differentiation activity detected by the above-mentioned method was found in the bound fraction. Therefore, the bound fraction was dialyzed against 20 mM Tris/HCl buffer (pH 7.4) and applied to a Q-Sepharose column equilibrated with the same buffer. The column was thoroughly washed and a megakaryocyte differentiation factor was eluted by NaCl gradient (see FIG. 1). This factor was eluted near the position of 0.3 to 0.5M NaCl.

Figure 2:
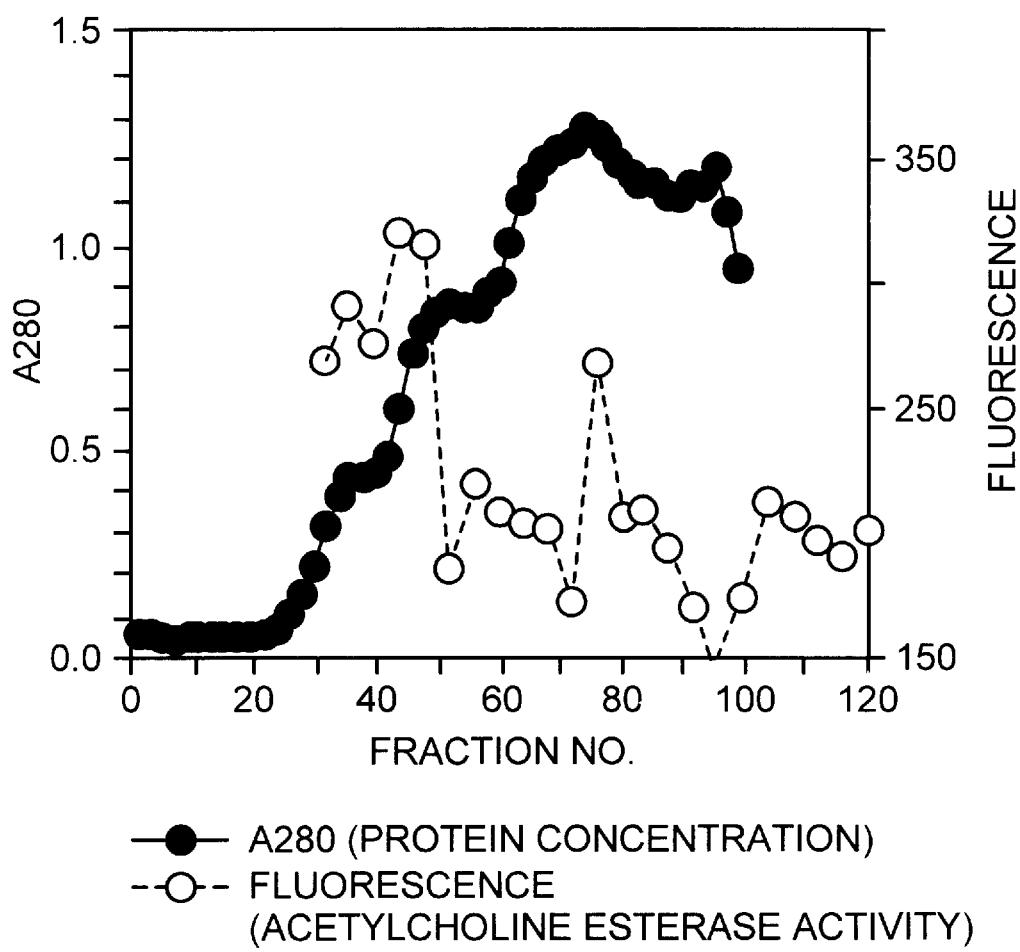
FIG. 2 shows an elution profile of protein (A280 —●—) and a megakaryocyte differentiation factor (acetylcholine esterase activity —○—) from a Phenyl-Sepharose column, wherein the elution was carried out by ammonium sulfate concentration gradient (30 to 0%) and ethyleneglycol concentration gradient (0 to 50%) to obtain fractions Nos. 1 to 100, followed by 50% ethyleneglycol to obtain fraction Nos. 101 to 120.

The active fraction obtained from Q-Sepharose was made ammonium sulfate 30% saturation, and was applied to a phenyl Sepharose column equilibrated with 20 mM Tris/HCl buffer (pH 7.4) containing 30% saturation of ammonium sulfate. The megakaryocyte differentiation factor was eluted by simultaneously forming concentration gradients of ammonium sulfate (30% to 0%) and ethyleneglycol (0 to 50%) (see FIG. 2). The megakaryocyte differentiation factor measured in the presence of anti-IL-6 antibody was observed over several fractions in the beginning of the concentration gradient formation.

Figure 3:
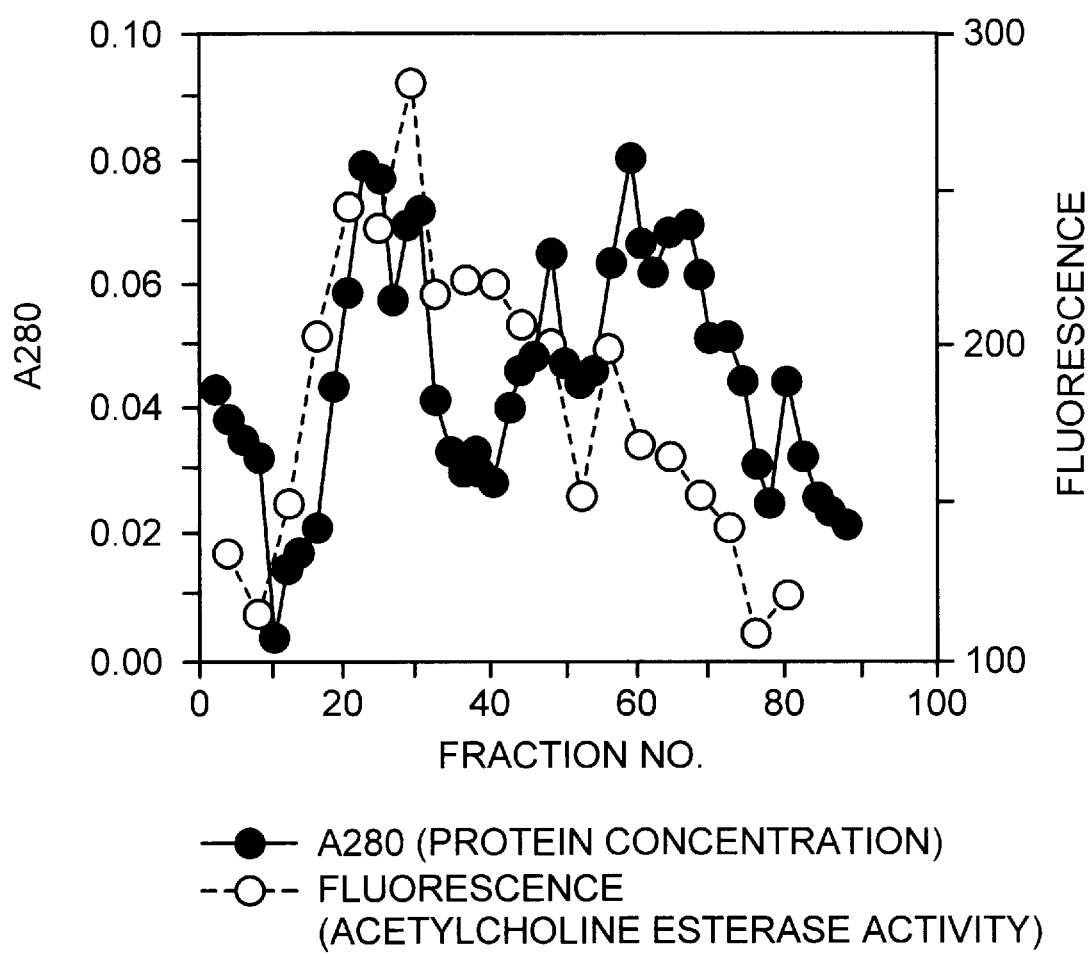
FIG. 3 shows an elution profile of protein (A280 —●—) and a megakaryocyte differentiation factor (acetylcholine esterase activity —○—) from an S-Sepharose column, wherein the elution was carried out by NaCl concentration gradient (0 to 0.5M) to obtain fractions Nos. 1 to 100.

The fractions thus obtained were combined, thoroughly dialyzed against 50 mM MES/NaOH buffer (pH 6.0), and applied to an S-Sepharose column equilibrated with the same buffer. A bound fraction was eluted by a 0 to 0.5M NaCl concentration gradient (see FIG. 3). Although activity was widely distributed, relatively high activity was found in the beginning of the concentration gradient formation. The fractions obtained from S-Sepharose were applied to a Hilord 26/60 Super Dex 75 (Pharmacia) column for gel filtration. The column used had be previously equilibrated with the same buffer, and elution was carried out with the same buffer (see FIG. 4). Activity of megakaryocyte differentiation activity was eluted near the position corresponding to a molecular weight of 55 to 57 kDa.

Figure 5:
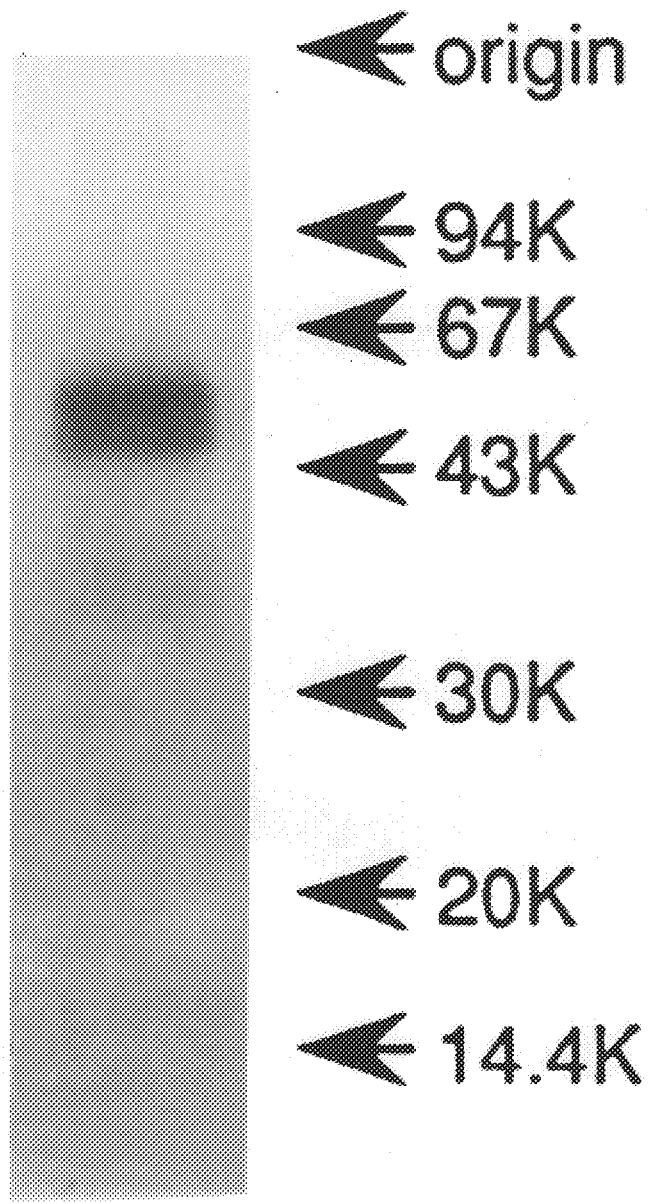
FIG. 5 is an electrophoretic pattern showing a result of SDS-PAGE analysis of the purified megakaryocyte differentiation factor.

According to the above-mentioned steps, about 80 μg of a fraction showing two bands near 55 to 57 kDa as analyzed by SDS-PAGE was obtained from 300 L of a culture supernatant of A431 derived cells (see FIG. 5). The two bands were correlated with the activity (FIG. 1). Accordingly, it was concluded that the two bands observed in said fraction correspond to a desired megakaryocyte differentiation factor.

(4) Properties of megakaryocyte differentiation factor

The present megakaryocyte differentiation factor has the following properties.

Figure 4A:
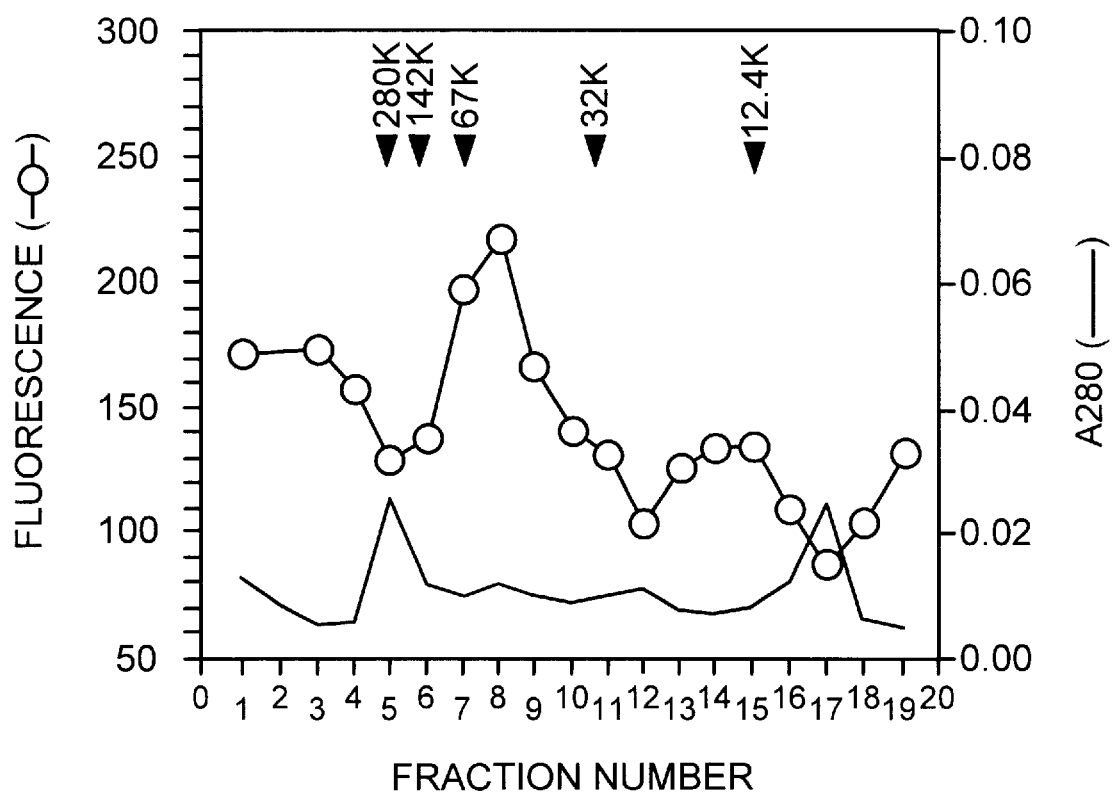
FIG. 4 shows an elution profile of protein (A280 ———) and megakaryocyte differentiation factor (acetylcholine esterase activity —○— ) from a Hiroad 26/60 Superdex 75 Pg column, and a result of analysis of the resulting fractions by SDS-PAGE (lower part of the Figure).
Figure 4B:
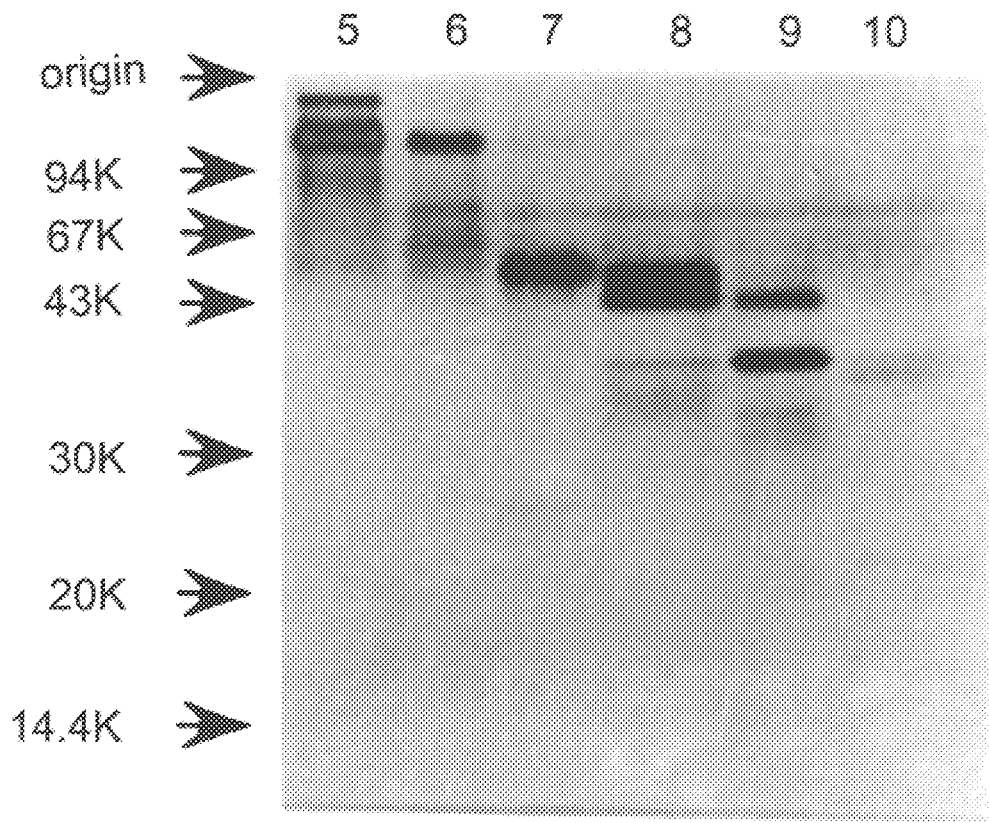

1) Molecular weight: about 55 kDa (gel filtration and SDS-PAGE) (FIGS. 4 and 5)

The present factor exhibits two bands in SDS-PAGE, and there is no difference in mobility between reducing condition and a non-reducing condition. Therefore the factor does not have intermolecular disulfide linkage.

Figure 6:
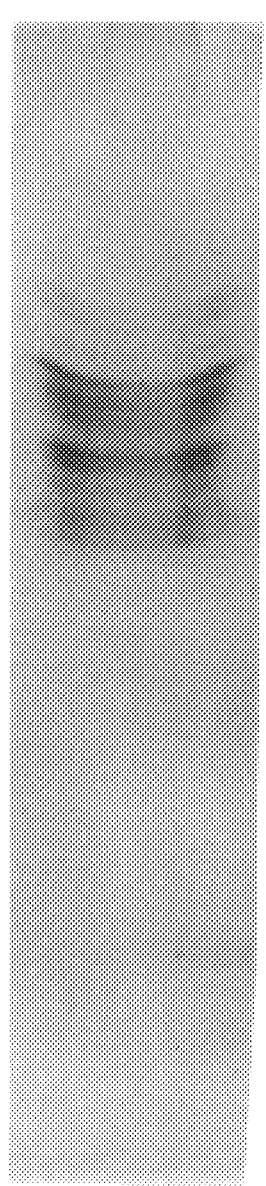
FIG. 6 shows a result of an isoelectric focusing of the purified megakaryocyte differentiation factor.

2) Isoelectric point: 6.5±0.5 (FIG. 6)

A several bands are observed in the above-mentioned range.

Figure 7:
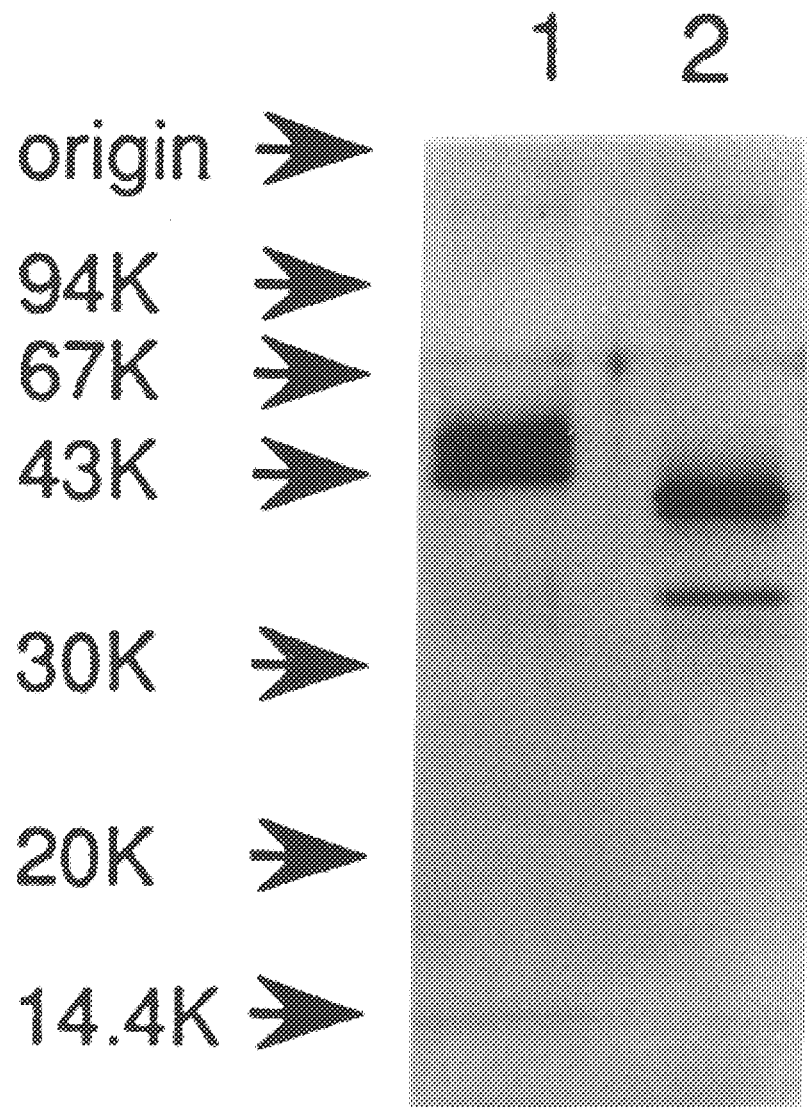
FIG. 7 is an electrophoretic pattern showing a result of sugar chain analysis for the purified megakaryocyte differentiation factor by SDS-PAGE, wherein the column 1 shows a result for a non-treated megakaryocyte differentiation factor, and the column 2 shows a result for an endoglycosidase F-treated megakaryocyte differentiation factor (note, the band near the 35 kD position is derived from the enzyme preparation).

3) The above-mentioned heterogeneity of the present factor can be explained as heterogeneity in a sugar chain structure of glycoprotein. Namely, where the present factor is treated with endoglycosidase F which is an asparagine linked sugar removing enzyme, the molecular weight of the present factor decreased to a molecular weight of about 40 kDa, and the heterogeneity also decreased (FIG. 7), in SDS-PAGE. In addition, where a fraction exhibiting a single band and a fraction exhibiting two bands were digested with API and a peptide map was prepared by fractionation by a reversed phase HPLC, the difference was not observed between the two fractions.

4) The present factor contains at least one of the amino acid sequences shown in SEQ ID NO: 1 to 9.

Figure 8:
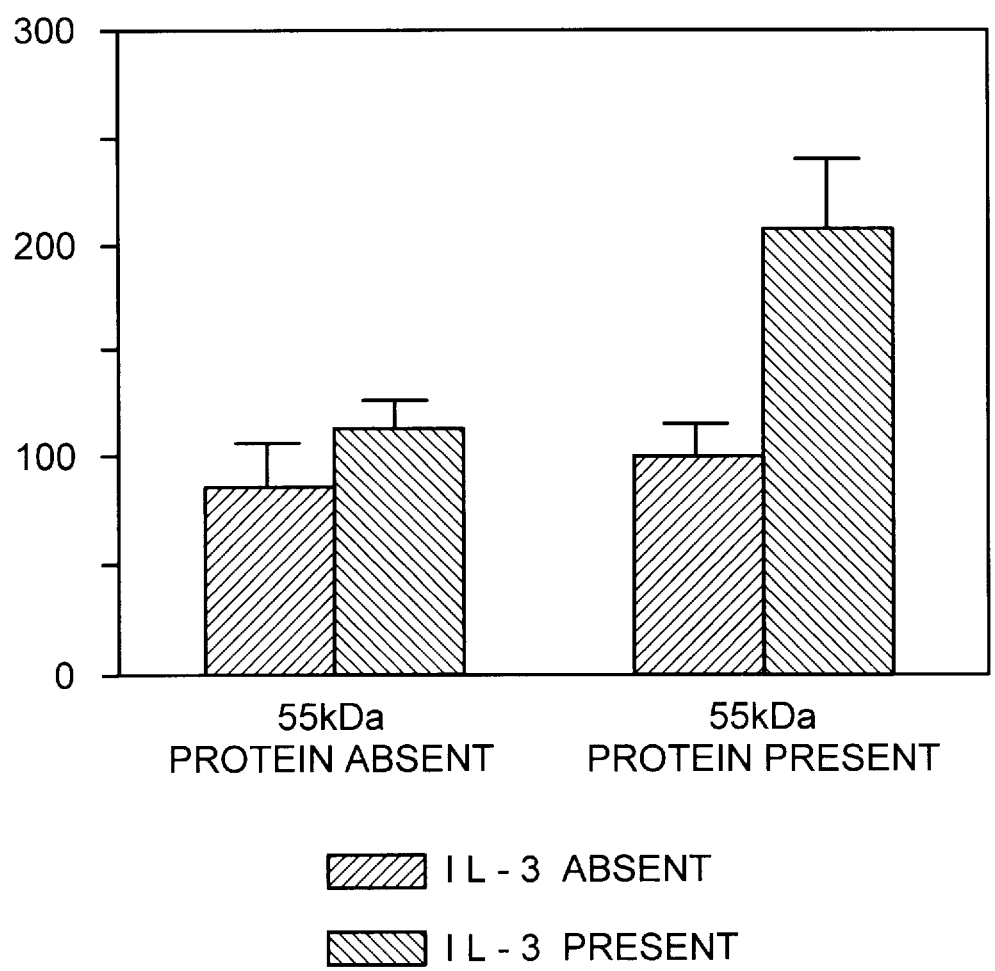
FIG. 8 is a graph comparing acetylcholine esterase activity of megakaryocytes derived from mouse bone marrow cells cultured for 5 days in the presence or absence of purified megakaryocyte differentiation factor (55 kDa protein) and with or without addition of IL-3.
Figure 9B:
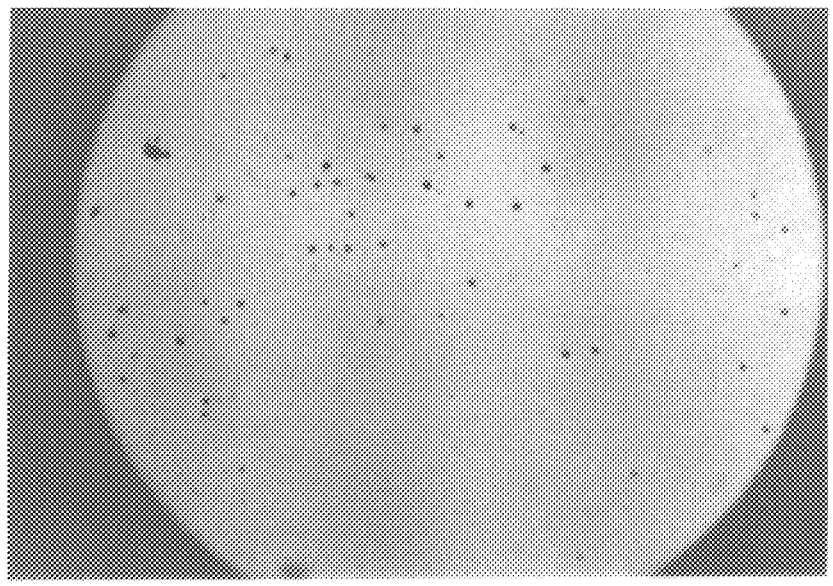
FIGS. 9A and 9B show a result of acetylcholine esterase staining of mouse bone marrow cells cultured for 4 days after the addition of IL-3, in the presence (B) or absence (A) of purified megakaryocyte differentiation factor.
Figure 9A:
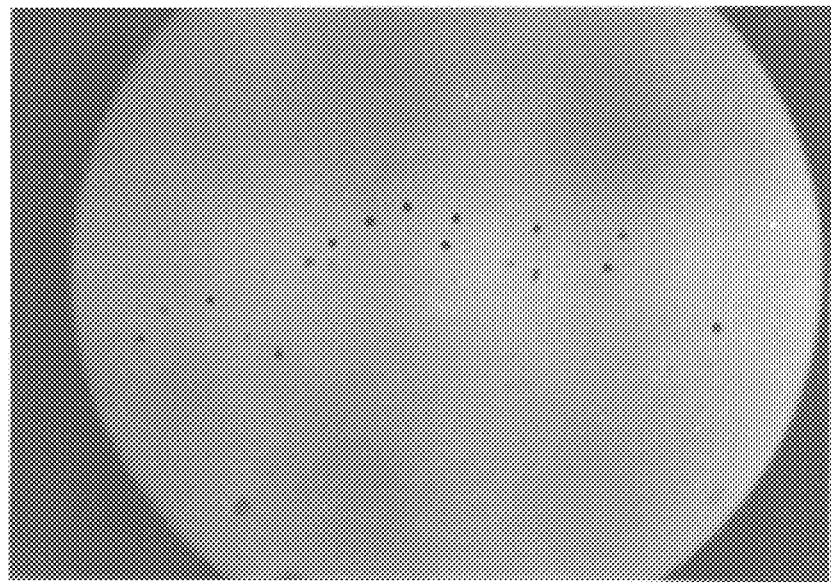
Figure 10B:
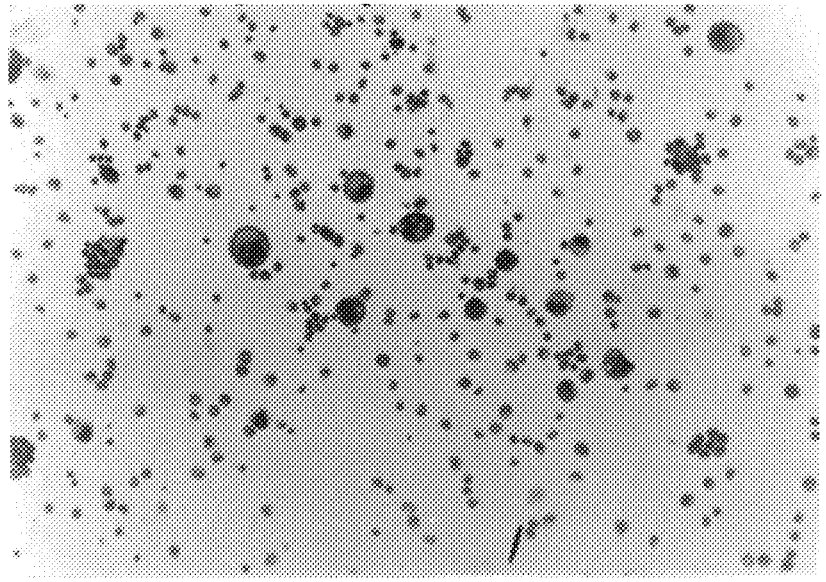
FIGS. 10A and 10B show a result of May-Gruenwald-Giemsa's staining of mouse bone marrow cells cultured for 4 days after the addition of IL-3, in the presence (B) or absence (A) of purified megacaryocyte differentiation factor.
Figure 10A:
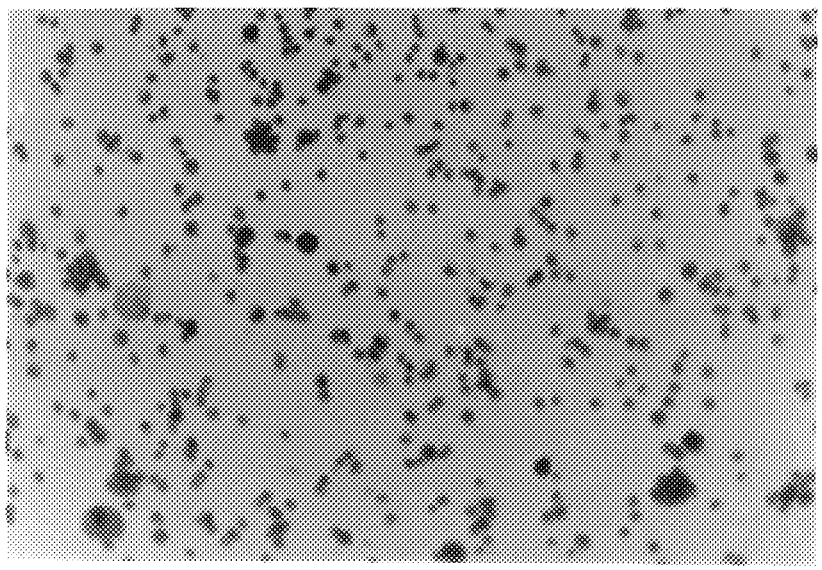

5) Biological activity

Where mouse bone marrow cells were cultured in the presence of a purified megakaryocyte differentiation factor and IL-3, the proliferation and differentiation of megakaryocytes are observed (FIGS. 8, 9 and 10). FIG. 8 shows the result of measurement for acetylcholine esterase activity of megakaryocytes; FIG. 9 shows the result of acetylcholine esterase staining of the cultured cells (×20); and FIG. 10 shows the result of May-Gruenwald-Giemsa's staining of the cultured cells (×100). In both the FIGS. 9 and 10, it is seen that megakaryocytes increased in the presence of a megakaryocyte differentiation factor (B) in comparison with in the absence of the same (A).

(5) Structure of megakaryocyte differentiation factor

To characterize the structure of a purified megakaryocyte differentiation factor, the factor was digested with API and the structures of the resulting fragments were determined. After the digestion of the factor with API, each fragment was recovered by reversed phase HPLC, and the structures for appropriate fractions were determined. As a result, the peptide fragments had amino acid sequences shown in SEQ ID NO: 1 to 9.

Example 2. Determination of Structure of CDNA for megakaryocyte differentiation factor 1. Analysis of cDNA nucleotide sequence of megakaryocyte differentiation factor by PCR (1)

Oligonucleotides NI065 (SEQ ID NO: 10; corresponding to 449–486 of SEQ ID NO: 30) and NI067 (SEQ ID NO: 11; corresponding to 1049–1080 of SEQ ID NO: 30) were synthesized by designing nucleotide sequences on the basis of the amino acid sequences shown in SEQ ID NO: 3 and 4 respectively.

Total RNA was purified from A431 cells using ISOGEN (Wako Pure Chemical) according to the manufacturer's instructions. RNA having poly A was purified from the total RNA, and a reaction was carried out using a 3'-RACE Kit (Gibco BRL). Namely, the above-mentioned oligomer NI065 and oligomer 3'-RACE adaptor primer (SEQ ID NO: 12) attached to the 3'-RACE Kit (Gibco BRL) were used to carry out polymerase chain reaction (PCR) according to instructions included with the kit.

The reaction product was then subjected to second PCR using the primer NI067 and the oligomer 3'-RACE adapter primer included in the 3'-RACE Kit (Gibco BRL) to obtain a DNA fragment of about 900 base pairs. Next, using a direct nucleotide sequence determination method for a PCR product, according to U. Gyllensten et. al., Proc. Natl. Acad. Sci. USA 85: 7652 (1988), the DNA fragment of about 900 base pairs was directly used as a reaction substrate to determine a nucleotide sequence of a portion representing protein and a portion downstream of the protein portion using a Taqu Dye Deoxy Terminator Cycle Sequencing kit available from Applied Biosystem and a fluorescent nucleotide sequencer (Applied Biosystem, Type 370A) according to the manufacture's instruction. As a result, a sequence from nucleotide number 1081 to 1950 of SEQ ID NO: 30 was shown.

On the basis of this sequence, oligomer KY100 (SEQ ID NO: 13; corresponding to 1255-1236 of SEQ ID NO: 30) was synthesized. The reaction product obtained by the PCR using NI065 and the oligomer 3'-RACE adapter primer attached to the 3'-RACE Kit (Gibco BRL) was used as a reaction substrate to carry out a further PCR using NI065 and KY100. As a result, a DNA fragment of 807 base pairs was obtained.

This DNA fragment of 807 base pairs was directly used as a reaction substrate to determine its nucleotide sequence using Taq Dye Deoxy Terminator Cycle Sequencing kit available from Applied Biosystem and a fluorescent nucleotide sequencer according to the manufacture's instruction. As a result, a nucleotide sequence from nucleotide number 487 to 1080 of SEQ ID NO: 30 was shown. On the basis of this sequence, oligomers NI073 (SEQ ID NO: 14; corresponding to 864–886 of SEQ ID NO: 30), NI074 (SEQ ID NO: 15; corresponding to 1012 to 992 of SEQ ID NO: 30), and NI075 (SEQ ID No: 16; corresponding to 802–782 of SEQ ID NO: 30) were synthesized.

2. Analysis of cDNA nucleotide sequence of megakaryocyte differentiation factor by PCR (2)

A. Preparation of mRNA from megakaryocyte differentiation factor expressing cell line (A431)

From 1.1 g of frozen cells of human epidermoid carcinoma cell line (A431), 25 μg of mRNA was extracted and purified using an RNA extraction kit and an mRNA purification kit available from Pharmacia-LKB.

B. Preparation of DNA phage library from megakaryocyte differentiation factor expressing cell line (A431)

(1) Synthesis of cDNA

From 5 μg of the mRNA derived from A431, cDNA was synthesized using a cDNA synthesis kit Time Saver available from Pharmacia-LKB. First 5 μg of mRNA dissolved in 20 μl of distilled water treated with diethylpyrocarbonate (DEPC) was heated at 65° C. for 10 minutes and cooled on ice. 11 μl of a first strand reaction mixture, 1 μl of DTT solution and 1 μl of 130 U/ml NotI/oligomer 18 primer solution (Pharmacia-LKB) were added thereto, and the mixture was incubated at 37° C. for an hour.

The reaction mixture was added to a second strand reaction mixture, and the mixture was incubated at 12° C. for 30 minutes and 22° C. for an hour, and heated at 65° C. for 10 minutes. 100 μl of a mixture of phenol/chloroform/isoanylalcahol (25:24:1; abbreviated as PC hereinafter) was added thereto, and the mixture was vigorously stired, centrifuged at 14,000×9 for one minute to obtain a supernatant, which was then fractionated by a Sephacryl S-400 spin column (Pharmacia LKB) to obtain 100 μl of cDNA solution.

(2) Addition of EcoRI adaptor

To 100 μl of the cDNA solution were added 5 μl of 10 U/ml EcoRI adaptor (Pharmacia LKB), 30 μl of polyethylene glycol buffer, 1 μl of ⅕ diluted ATP solution and 1 μl of T4 DNA ligase, and the mixture was incubated at 37° C. for an hour. After heating at 65° C. for 10 minutes, 1.5 μl of ATP solution and 1 μl of T4 polynucleotide kinase were added thereto and the mixture was incubated at 37° C. for 30 minutes. After heating at 65° C. for 10 minutes, 2 μl of 20 U/μl NotI was added to the mixture, which was then incubated at 37° C. for an hour. 150 μl of PC was added to the mixture, which was then vigorously stirred and centrifuged at 14,000×g for a minute, and the supernatant was fractionated on Sephadex S-400 spin column to obtain 150 μl of cDNA solution.

(3) Incorporation of cDNA into phage vector and in vitro packaging

After digesting with EcoRI and NotI, to 15 μl of the cDNA solution were added 2 μg of dephosphorylated λgt11D (Pharmacia LKB). After ethanol precipitation, the precipitate was dissolved in 8 μl of ligase buffer solution, and 1 μl of ⅕-diluted ATP solution and 1 μl of T4 DNA ligase were added to the solution, which was then incubated at 16° C. for 30 minutes and stored on ice.

An in vitro packaging reaction was carried out using Gigapack II Gold (Stratagene), and a library of $3.22 \times 10^6$ pfu of recombinant phages was obtained from said 3 ligase reaction products. Said library was amplified in an E. coli Y1090 r⁻ host to obtain $6.0 \times 10^{10}$ pfu/ml of an A431 phage library stock.

C. Identification and isolation of cDNA fragment for megakaryocyte differentiation factor by PCR (1) Amplification of cDNA insert fragment in A431 phage library by PCR 10 μl of a stock solution of $6.0 \times 10^{10}$ pfu/ml A431 phage library (corresponding to $6.0 \times 10^8$ pfu) was used as a template DNA for PCR reaction, and 5 μl of 10× PCR buffer, 8 μl of 1.25 mM 4 dNTPs, 2 μl of 1 OD/ml λgt11-forward primer (λgt 11F) (SEQ ID NO: 17), 2 μl of 1 OD/ml λgt11-reverse primer (λgt 11R) (SEQ ID NO: 18), and 1 μl of 5 U/μl Taq DNA polymerase (Perkin Elmer Cetus) were added, and the total volume of the mixture was made to be 50 μl with DEPC-treated distilled water. 30 reaction cycles of 93° C. for a minute, 55° C. for 2 minutes and 72° C. for 3 minutes were carried out, and the reaction mixture was incubated at 72° C. for 10 minutes. As a result of an analysis by 1% Agarose gel electrophoresis, a smeary pattern ranging 0.8 to 6 kb was shown.

(2) PCR analysis using cDNA insert DNA amplification fragment mixture as a template and using TP7 (SEQ ID NO: 20; corresponding to 683–703 of SEQ ID NO: 30), /TP10, TP7/TP6 (SEQ ID NO: 19; corresponding to 1036–1001 of SEQ ID NO: 30), TP8 (SEQ ID NO: 21; corresponding to 941–964 of SEQ ID NO: 30), TP10 (SEQ ID NO: 22; corresponding to 1036–986 of SEQ ID NO: 30) and TP8/TP6 as primers 1 μl of a ⅕₀₀₀-diluted solution of the above-mentioned PCR reaction product was used as a template DNA for PCR reaction, and 5 μl of 10× PCR buffer, 8 μl of 1.25 mM 4 dNTPs, 2 µl each of 1 OD/ml primers in combination as described hereinafter and 1 µl of Perfect Match (Stratagene) were added, and a total volume of the mixture was made to 49 µl with DEPC-treated distilled water.

The reaction mixture was heated at 95° C. for 5 minutes and 60° C. for 5 minutes, 1 µl of 5 U/µl Taq DNA polymerase (Perkin Elmer Cetus) was added thereon, and 30 cycles of 94° C. for a minute, 60° C. for 2 minutes and 72° C. for 3 minutes were carried out, followed by an incubation at 72° C. for 10 minutes. As primers, TP7/TP10, TP7/TP6, TP8/TP10, and TP8/TP6 were used.

As a result of an analysis of the PCR reaction product by 2% agarose gel electrophoresis, bands of 354 bp, 354 bp, 96 bp and 96 bp were obtained corresponding to primers respectively.

(3) Analysis for primary sequence of PCR amplification products (354 bp) obtained by using primers TP7/TP10 and TP7/TP6

The bands of said PCR amplification products (354 bp) obtained using primers TP7/TP10 and TP7/TP6 were excised from the 2% agarose gel after the electrophoresis, and to the excised agarose gel pieces was added 50 µl of DEPC-treated distilled water, and the mixture was heated at 45° C. for 30 minutes. To 2 µl of this solution as a template DNA, were added 5 µl of 10× PCR buffer, 8 µl of 1.25 mM 4 dNTPs, 2 µl each of 1 OD/ml primers in combination and 1 µl of Perfect Match (Stratagene), and a total volume of the reaction mixture was made to 49 µl with DEPC-treated distilled water. The mixture was heated at 95° C. for 5 minutes and 60° C. for 5 minutes, 1 µl of 5 U/µl Taq DNA polymerase (Perkin Elmer Cetus) was added, and 30 reaction cycles of 94° C. for a minutes, 60° C. for 2 minutes and 72° C. 3 minutes were carried out, followed by incubation at 72° C. for 10 minutes. As primes for the above-mentioned PCR reaction, TP7/TP10 and TP7/TP6 were used. Bands of the PCR reaction products (each 354 bp) were excised from 2% agarose gel of the electrophoresis, extracted and purified, and the product was inserted into pCR II (Invitrogen), which was then used to transform E. coli INVαF' (Invitrogen). Plasmid DNA was extracted and purified, and it was confirmed by EcoRI digestion that DNA fragment of 354 bp had been inserted.

Primary sequence of the DNA insert fragment was analyzed using M13 forward primer (M13F) (SEQ ID NO: 23) and M13 reverse primer (M13R) (SEQ ID NO: 24) (Aplied Biosystem's automated sequencer, Model 370A). As a result, a 296 bp sequence corresponding to the nucleotide number 704 to 999 of SEQ ID NO: 30 was found, and this sequence contained C-terminal 3 amino acids (XRK; but ERK from DNA nucleotide sequence) of SEQ ID NO: 9 corresponding to the downstream portion of primer TP7, N-terminal 5 amino acids (ADLSG) of SEQ ID NO: 6 corresponding to the upstream portion of primer TP6, and 8 amino acids (YLRALGLK) of SEQ ID NO: 5 corresponding to primer TP8, revealing that the PCR reaction products (each 354 bp) is a part of cDNA coding for megakaryocyte differentiation factor.

3. Screening of cDNA coding for megakaryocyte differentiation factor

A. Preparation of cDNA plasmid library from megakaryocyte differentiation factor expressing cell line (A431)

(1) Synthesis of first strand cDNA From 5 µg of mRNA derived from A431 cell line, cDNA was synthesized using a Super Script plasmid system available from GIBCO. First 2 µl of NotI primer adaptor was added to 5 µg of mRNA dissolved in 5 µl of diethylpyrocarbonate (DEPC)-treated distilled water, and the mixture was heated at 70° C. for 10 minutes and cooled on ice. 4 µl of 5× first strand buffer, 2 µl of 0.1M DTT solution, 1 µl of 10 mM 4dNTPs and 1 µl of DEPC-treated distilled water were added thereto, and the mixture was incubated at 37° C. for 2 minutes. 5 µl of a Super Script reverse transcriptase was added to the reaction mixture, which was then incubated at 37° C. for one hour and then put on ice to stop the reaction.

(2) Synthesis of second strand cDNA

To 18 µl of 20 µl reaction mixture for the first strand cDNA synthesis were added 93 µl of DEPC-treated distilled water, 30 µl of 5× second strand buffer, 3 µl of 10 mM 4 NTPs, 1 µl of 10 U/µl E. coli DNA ligase, 4 µl of 10 U/µl E. coli DNA polymerase and 1 µl of 2 U/µl E. coli RNase H, and the mixture was incubated at 16° C. for 2 hours. 2 µl (10 U) of T4 DNA polymerase was added to the reaction mixture, which was then incubated at 16° C. for 5 minutes.

The reaction mixture was put on ice, and after adding 10 µl of 0.5M EDTA and 150 µl of PC thereto, was vigorously stirred and centrifuged at 14,000×g for 10 minutes, and 140 µl of the supernatant was transferred to a fresh centrifuge tube. 70 µl of 7.5M ammonium acetate and 0.5 ml of ethanol were added to the supernatant, which was then allowed to stand at −80° C. for 30 minutes. The mixture was centrifuged at 14,000×g for 10 minutes, and after removing the supernatant, the precipitate was washed with 0.5 ml of 70% ethanol and dried under a reduced pressure.

(3) Addition of BstXI adapter

The above-mentioned cDNA precipitate was dissolved in 25 µl of DEPC-treated distilled water, 10 µl of 5×T4 DNA ligase buffer, 10 µl of BstXI adapter (Invitrogen) and 5 µl of T4 DNA ligase were added to the solution, which were then incubated at 16° C. for 16 hours. 50 µl of PC was added to the mixture, which was the vigorously stirred, and centrifuged at 14,000×g for 5 minutes. 45 µl of the supernatant was transferred to a fresh centrifuge tube. 25 µl of 7.5M ammonium acetate and 150 µl of ethanol were added to the tube, which was stirred and allowed to stand at −80° C. for 30 minutes. After centrifuging at 14,000×g for 10 minutes to remove supernatant, the precipitate was washed with 0.5 ml of 70% ethanol and dried under a reduced pressure.

(4) NotI digestion

The above-mentioned cDNA precipitate was dissolved in 41 µl of DEPC-treated distilled water, and 5 µl of REAct 7 buffer and 4 µl of NotI were added to the solution, which was incubated at 37° C. for 2 hours. 50 µl of PC was added to the mixture, which was then vigorously stirred and centrifuged at 14,000×g for 10 minutes, and 45 µl of the supernatant was transferred into a centrifuge tube.

(5) Elimination of adapter and size fractionation of partial cDNA

The above-mentioned cDNA solution was fractionated using a Quick Spin Column Linker 5 (Boehringer Mannheim). 50 µl of 40 µg/µl cDNA was obtained.

(6) Incorporation of cDNA into phagevector and transformation of E. coli

To 37.5 µl of the above-mentioned cDNA solution were added 12.5 µl of pCR/CMV (Invitrogen) vector (29 µg/µl) digested with Not I and BstXI, and further added were 400 µl of Takara Ligation kit A solution and 50 µl of B solution, and the mixture was incubated at 16° C. for 30 minutes, and 1 ml of Max Efficiency DH5α competent cells (BRL) were transformed to obtain 71,550 recombinant clones. All colonies were collected from plate (2.86×10$^7$ cells/ml) and stored at −80° C. in the presence of 20% glycerol.

B. Screening of megakaryocyte differentiation factor cDNA by colony hybridization Using the cDNA plasmid library derived from A431 cell line, a total of 227,000 (3700/plate) colonies were formed on 60 plates of 9 cm diameter, and the colonies were replicated to nitrocellulose filters. A probe was prepared by carrying out PCR (as described hereinbefore) using primer NI 067 and 3'-RACE adaptor (GIBCO BRL) to obtain a 900 bp PCR product, digesting the PCR product with Bam HI to obtain two DNA fragments (0.5 kb and 0.4 kb) and nick-translating the DNA fragments with [$\alpha$-$^{32}$P]dCTP.

For the colony hybridization, the filter was incubated in 5× SSC, 25 mM phosphate buffer (pH 7.4), 5× Denhaldt's solution, 1% SDS, 100 μg/ml heat denatured salmon sperm DNA and 50% formamide at 42° C. for 18 hours, and washed with 5× SSC, 0.1% SDS at 40° C. for 20 minutes and 45° C. for 20 minutes. Detection was carried out by exposing BAS 2000 (Fuji Film) for 18 hours.

First, second and third screening was carried out to obtain 4 clones, i.e., TP290, TP308, TP310 and TP317. The length of insert cDNA was 1.2 kb, 1.1 kb, 1.2 kb and 1.2 kb respectively. The TP290, TP310 and TP317 cover a region downstream from the nucleotide number 685 of SEQ ID NO: 30.

4. Analysis of cDNA nucleotide sequence coding for meqakaryocyte differentiation factor by PCR (3)

A. Preparation of mRNA from megakaryocyte differentiation factor expressing cell line (HPC-Y11)

From 1.1 g of frozen cells of human pancreatic cancer cell line (HPC-Y11), 50 μg of mRNA was extracted and purified using an RNA extraction kit and mRNA purification kit available from Pharmacia-LKB.

B. Preparation of cDNA phage library from megakaryocyte differentiation factor expressing cell line (HPC-Y11)

(1) Synthesis of cDNA

From 5 μg of mRNA derived from HPC-Yll, cDNA was synthesized using a Pharmacia-LKB's Time Saver cDNA synthesis kit. First, 5 μg of mRNA was dissolved 20 μl of diethylpyrocarbonate (DEPC)-treated distilled water, and the solution was heated at 65° C. for 10 minutes and cooled on ice. 11 μl of first strand reaction mixture, 1 μl of DTT solution and 1 μl of NotI/oligomer 18 primer solution were added to the mixture, which was then incubated at 37° C. for an hour.

100 μl of second strand reaction mixture was added to the mixture, which was then incubated at 12° C. for 30 minutes and at 22° C. for an hour, and heated at 65° C. for 10 minutes. 100 μl of phenol-chloroform-isoamyl alcohol (25:24:1, abbreviated as PC) was added to the mixture, which was then vigorously stirred and centrifuged at 14,000×g for a minute, and the supernatant was fractionated using a Sephacryl S-400 spin column (Pharmacia-LKB) to obtain 100 μl of cDNA solution.

(2) Addition of EcoRI adaptor

To 100 μl of the cDNA solution, were added 5 μl of EcoRI adapter (Pharmacia-LKB), 30 μl of polyethylene glycol, 1 μl of ATP solution and 1 μl of T4 DNA ligase, and the mixture was incubated at 37° C. for an hour. After heating at 65° C. for 10 minutes, 1.5 μl of ATP solution and 1 μl of T4 polynucleotide kinase were added to the mixture, which was then incubated at 37° C. for 30 minutes. After heating at 65° C. for 10 minutes, 12 μl of Not I was added to the mixture, which was then incubated at 37° C. for an hour. 150 μl of PC was added to the mixture, which was then vigorously stired. and centrifuged at 14,000×g for a minute, and the supernatant was fractionated using a Sephacryl S-400 spin column to obtain 150 μl of cDNA solution.

(3) Incorporation of cDNA into phage vector and in vitro packaging

To 15 μl of the cDNA solution, was added 2 μg of λgt 11D (Pharmacia-LKB) which had been digested with EcoRI and Not I and dephosphorydated, and after ethanol precipitation, the precipitate was dissolved in 8 μl of ligase buffer. 1 μl of ⅕-diluted ATP solution and 1 μl of T4 DNA ligase were added to the mixture, which was then incubated at 16° C. for 30 minutes and stored on ice. An in vitro packaging reaction was carried out using a Giga Pack II Gold (Strotagene), and 5.34×10$^6$ pfu of recombinant phages were obtained from the above-mentioned 3 ligase reaction products. The library was amplified in *E. coli* Y1090 r$^{-1}$ host to obtain a stock of 1.7×10$^{11}$ pfu/ml HPC-Y11 phage library.

C. Identification and isolation of 5'-portion of megakaryocyte differentiation factor cDNA (1) Amplification by PCR of HPC-Y11 phage library cDNA insert DNA fragment primer NI074 upstream portion.

To 1 μl (corresponding to 1.7×10$^9$ pfu) of 6.0×10$^{10}$ pfu/ml HPC-Y11 phage library stock solution as a template DNA for PCR reaction, were added 5 μl of 10× PCR buffer, 8 μl of 1.25 mM 4 dNTPs, 1 μl of 10 OD/mlλgt11-forward F1 primer (SEQ ID NO: 25), 1 μl of 50 D/ml NI074 primer and 1 μl of Perfect Match (Stratagene), and a total volume was made to be 49 μl with DEPC-treated distilled water.

After heating the reaction mixture at 95° C. for 5 minutes and 60° C. for 5 minutes, 1 μl of 5 U/μl Taq DNA polymerase (Perkin Elmer Cetus) was added thereto, and 35 reaction cycles of 94° C. for a minute, 60° C. for a minute and 72° C. for 2 minutes were carried out, followed by incubation at 72° C. for 10 minutes. A result of analysis by 2% agarose gel electrophoresis showed a smeary pattern ranging from 0.3 to 6 kb.

(2) PCR analysis using a template which is a PCR amplification fragment mixture prepared by using λgt11F1/NI074 primer, and using as primers λgt11F2 (SEQ ID NO: 26)/NI075, λgt11F2/TP12 (SEQ ID NO: 28; corresponding to 703–683 of SEQ ID NO: 30), λgt11F2/TP11 (SEQ ID NO: 27; corresponding to 619–599 of SEQ ID NO: 30), λgt11F2/TP13 (SEQ ID NO: 29; corresponding to 595–575 of SEQ ID NO: 30), TP7/NI074, TP7/NI075, and NI073/NI074

1 μl of a 1/100 diluted solution of the above-mentioned PCR reaction product was used for a template DNA for PCR reaction, and 5 μl of 10× PCR buffer, 8 μl of 1.25 mM 4 dNTPs, 0.5 μl each of 10 OD/ml primers in combination as described hereinafter, and 1 μl of Perfect Match (Stratagene) were added thereto, and a total of the reaction mixture was made to be 49 μl with DEPC-treated distilled water. The reaction mixture was heated at 95° C. for 5 minutes and at 60° C. for 5 minutes, 1 μl of 5 U/μl Taq DNA polymerase (Perkin Elmer Cetus) was added thereto, and 35 reaction cycles of 94° C. for a minute, 60° C. for 2 minutes and 72° C. for 2 minutes were carried out, followed by an incubation at 72° C. for 10 minutes.

As primers, λgt11F2/NI075, λgt11F2/TP12, λgt11F2/TP11, λgt11F2/TP13, TP7/NI074, TP7/NI075, and NI073/NI074 were used. As a result of 2% agarose gel electrophoresis, bands of 969 bp, 870 bp, 786 bp, 762 bp, 330 bp, 120 bp and 149 bp were obtained corresponding to the primers.

(3) PCR analysis and primary sequence analysis using λgt11F/TP11 and λgt11F/TP13 primer, for PCR amplification product (969 bp) prepared using F2/NI075 primers 0.5 μl of the above mentioned PCR reaction product (969 bp) prepared by using λgt11F2/NI075 as primers was used as a template DNA for PCR reaction, and 5 μl of 10× PCR buffer, 8 μl of 1.25 mM 4 dNTPs, 1 μl of 10 OD/ml λgt11F primer, 1 μl of 10 OD/ml TP11 primers or 1 μl of 10 OD/ml TP13 primers, and 1 μl of Perfect Match (Stratagene) were added, and the total volume was made to be 49 μl with DEPC-treated distilled water.

The reaction mixture was heated at 95° C. for 5 minutes and 60° C. for 5 minutes, 1 μl of 5 U/μl Taq DNA polymerase (Perkin Elmer Setus) was added thereto, and 35 reaction cycles of 94° C. for a minute, 60° C. for 2 minutes and 72° C. for 2 minutes were carried out, followed by an incubation at 72° C. for 10 minutes.

Bands of PCR reaction products (678 bp and 654 bp, respectively) were excised from 2% agarose gel after electrophoresis, extracted and purified, and inserted into PCRII (Invitrogen), which was then used to transform *E. coli* IN VαF' (Introgen). Plasmid DNA was extracted and purified from the transformant, and digested with EcoRI to confirm that a 0.7 kb DNA fragment was inserted. The primary sequence of the inserted DNA fragment was analyzed by using M13 forward primer M13F and M13 reverse primer M13R (Applied Biosystems automated sequencer Model 370A).

As a result, a sequence of 619 bp corresponding to nucleotide number 1 to 619 of SEQ ID NO: 30 was found, and the nucleotide sequence of 133 nucleotides consisting of nucleotide number 487 to 619 of SEQ ID NO: 30 conformed to the N-terminus of the primary sequence found in Example 2.1. In this 619 bp sequence there are 19 amino acids of SEQ ID NO: 3 (VERVDFTNHLEDTR RNINK from DNA nucleotide sequence) and 5 amino acids (LYDAK) of SEQ ID NO: 7, and it was clarified that this PCR reaction products (each 0.7 kb) was a part of cDNA coding for megakaryocyte differentiation factor.

It was considered that the translation starting methionine corresponds to 74th nucleotide, and 5'-non translational region consisted of 73 bp. Accordingly, it was clarified that these PCR reaction products (each 0.7 kb) contain N-terminus of structural gene for megakaryocyte differentiation factor.

5. Analysis of cDNA nucleotide sequence coding for megakaryocyte differentiations factor by PCR (4)

Among an N-terminal portion of structural gene for a megakaryocyte differentiation factor derived from HPC-Y11 and a sequence considered to be a 5'-non-translational region, obtained in the section C(3), the sequence of nucleotide numbers 12 to 31 of SEQ ID NO: 30 which is a sequence part considered to be a 5'-non-translational region was used as a basis to synthesize an oligomer NI 083 (SEQ ID NO: 31).

The RNA having poly A prepared from A431 cells in the section 1., a Preamplification System (Gibco BRL) and random hexamers attached to the System were used to synthesize first strand cDNA according to included instructions, and PCR was carried out by using NI083 and NI074 as well as Ampli Taq (Takara). As a result, a DNA fragment of 1001 bp which is a cDNA fragment for a megakaryocyte differentiation factor was obtained.

This DNA fragment, a PCR product, of 1001 bp was directly used as a substrate for sequencing on a Taq Dye Deoxy Terminator Cycle Sequencing kit (Applied Biosystem) and a fluorescent sequencer (Applied Biosystem Type 370A) according to the included manufacturers instruction. As a result, a sequence of nucleotide numbers 32–486 of SEQ ID NO: 30 was found. In addition, a result obtained for nucleotide numbers 487 to 991 of SEQ ID NO: 30 conformed to the sequence obtained in the section 1.

By combining with the sequence obtained in the section 1., the nucleotide sequence 32–1950 of SEQ ID NO: 30 which is cDNA nucleotide sequence coding for a megakaryocyte differentiation factor of A431 cell was determined.

For this nucleotide sequence, all of possible 3 reading frames were mechanically translated into amino acid sequences and it was found that one of them has a region which can be translated to a continuing amino acid sequence containing all the amino acid sequences shown in SEQ ID NO: 1 to 9, and the reading frame of the megakaryocyte differentiation factor was determined.

It was found that in this reading frame a codon for methionine (nucleotide numbers 74 to 76) found at a translation start position exists, and from this position a region which can be translated to an amino acid sequence containing the amino acid sequences shown in SEQ ID NO: 1 to 9 continues up to the nucleotide position 1213 of SEQ ID NO: 30, and it was determined that the nucleotide sequence from the position 74 to the position 1213 of SEQ ID NO: 30 is the region translated to megakaryocyte differentiation factor.

The nucleotide sequence GCAATGG (nucleotide numbers 71 to 77 of SEQ ID NO: 30) encompassing the methionine codon of nucleotide numbers 74 to 76 of SEQ ID NO: 30 corresponds to a sequence (G/A-N-N-A-T-G-G) encompassing a methionine codon frequently present at a translation start site found by M. Kozak, Nucleic Acids Research (1981) Vol. 9, p5233–5252.

Primary sequence of megakaryocyte differentiation factor was thus clarified, the number of amino acids was 380 in the structural gene, an expected molecular weight was 42904.43, and an expected isoelectric point was 6.79. SEQ ID NOS: 1–6 and 9 give the partial amino acid sequences of peptide fragments recovered by reversed phase HPLC following digestion. After cloning the DNA sequence, the complete sequences of these peptides were determined to be that of amino acids 188–196, 181–197, 126–144, 325–341, 289–297, 305–324, and 204–213, respectively, of SEQ ID NO: 34. SEQ ID NOS: 7 and 8 correspond to amino acids 121–125 and 284–288, respectively, of SEQ ID NO: 34. In addition, A poly A addition signal AATAAA sequence is present at nucleotide numbers 1933 to 1998 of SEQ ID NO: 30.

Example 3.

Isolation and identification of cDNA coding for megakaryocyte differentiation factor from A431 by PCR and construction of expression vector Oligomers NI078 (SEQ ID NO: 32) and NI079 (SEQ ID NO: 33) were synthesized on the basis of the sequence (SEQ ID NO: 30) obtained in Example 2. Note in the NI078, the sequence of nucleotide numbers 13 to 37 encompassing the translation start methionine codon conforms to the sequence of the nucleotide numbers 74 to 98 of SEQ ID NO: 30 and an EcoRI recognizing site (nucleotide numbers 4 to 9) and an Nru I recognizing site (nucleotide numbers 8 to 13) were artificially added; and in the NI079, the sequence of the nucleotide numbers 17 to 49 conforms to the nucleotide sequence of the nucleotide numbers 1237 to 1269 of SEQ ID NO: 30, and an EcoRI recognizing site (nucleotide numbers 3 to 8) and an Not I recognizing site (nucleotide numbers 9 to 16) were artificially added.

The RNA having poly A prepared from A431 cells in Example 2 section 1., a Preamplification System (Gibco BRL), and Oligomers, i.e., random hexamers included in the system were used according to the included manufacturer's instructions to synthesize first strand cDNA, and PCR was carried out using the synthesized DNA as a template and NI078 and NI079 as primers and using Ampli Taq (Perkin Elmer Cetus). As a result, a DNA fragment of 1224 base pairs which is a cDNA fragment for a megakaryocyte differentiation factor and has all information relating to megakaryocyte differentiation factor, was obtained.

This DNA fragment was treated with EcoRI to generate EcoRI cohesive sites at both the ends of the cDNA coding for a megakaryocyte differentiation factor in virtue of EcoRI recognizing sites artificially added to the oligomers NI078 (SEQ ID NO: 32) and NI079 (SEQ ID NO: 33). This cDNA fragment coding for megakaryocyte differentiation factor was introduced into a mammalian expression vector pdKCR-DHFD at its EcoRI recognizing site to obtain pdKCR-DHFR-TPO55.

The animal cell expression vector pdKCR-dhfr (Oikawa, S. et. al., Biochem. Biophys. Res. Commun. 164, 39, 1989) is a derivative of pKCR (O' Hare et. al., Pro. Natl. Acod. Sci. USA, 78, 1527, 1981) and has SV40 early promoter and a rabbit β-globin gene and dhfr (dehydrofolate reductase) gene. Note, a host transformed with the expression vector, was designated as Escherichia coli SBM 308, and deposited with the Fermentation Research Institute, Agency of Industrial Science and Technology, 1–3, Higashi 3-chome, Tsukubashi, Ibaraki, Japan as FERM P-11506 on Jun. 7, 1990, and transferred to an international deposition under the Budapest treaty as FERM BP-4197 on Feb. 18, 1993.

The clone pdKCR-DHFR-TPO55 containing megakaryocyte differentiation factor cDNA which was incorporated into pdKCR-DHFR was sequenced using a Taq Dye Deoxy Terminator Cycle Sequencing kit (Applied Biosystem) and a fluorescent sequencer (Applied Biosystem Type 370A) according to included instructions. As a result, the determined nucleotide sequence conformed to the sequence of the nucleotide numbers 99 to 1236 of SEQ ID NO: 30 and oligomers NI078 and NI079. In addition, it was confirmed by the sequencing that a megakaryocyte differentiation factor cDNA inserted into the vector is in correct orientation in relation to an expression vector promoter.

As shown in the above, once the information of SEQ ID NO: 30 is provided, it is easy for a person skilled in the art that the nucleotide sequence is determined by amplifying cDNA coding for megakaryocyte differentiation factor in total or in a optional portion on megakaryocyte differentiation factor expressing cell line (for example, A431) and cloned in a optional expression vector.

Example 4.

Expression of megakaryocyte differentiation factor in Bombyx mori (1) Construction of Bombyx mori expression vector A megakaryocyte differentiation factor cDNA clone pdKCR-DHFR-TP055 was digested with NotI to cleave the NotI recognizing site artificially added to the NI079. The NotI cohesive end thus generated was blunt-ended using a blunting kit available from Takara Shuzo, and to the blunt end was added an XbaI linker (Takara Shuzo) according to an attached instruction. The plasmid thus obtained was digested simultaneously with NruI and XbaI to cleave the NruI recognizing site artificially added to the NI078 and the XbaI recognizing site of the XbaI linker introduced to prepare a megakaryocyte differentiation factor cDNA fragment having an NurI cohesive end and an XbaI cohesive end. This DNA fragment was inserted at the Nru I recognizing site into a baculovirus transfer vector for Bombyx mori nuclear polyhedrosis virus, pBm4 (available from Department of Insect Genetics and Bleeding National Institute of Sericultural and Entomological Science, Ohwashi, Tukuba, Ibaraki 305, Japan) simultaneously digested with NruI and XbaI to obtain pBm4-TPO55.

(2) Construction of TP055 recombinant virus

A cell line derived from Bombyx mori embryonic, BoMo15AIIc (available from Department of Insect Genetics and Bleeding National Institute of Sericultural and Entomological Science, Ohwashi, Tukuba, Ibaraki 305, Japan) was subcultured in a medium containing 10% fetal bovine serum (FBS: GIBCO BRL) and 500 $\mu$g/ml gentamicin in MGM 448 at 25° C. TP055 recombinant virus was constructed by co-introducing Bombyx mori nuclear polyhedrosis virus gene DNA and pBm4-TP055 plasmid DNA into Bombyx mori cultured cells by, for example, calcium phosphate co-precipitation method.

Namely, 2 $\mu$g of genomic DNA of wild type virus B6E (available from Department of Insect Genetics and Bleeding National Institute of Sericultural and Entomological Science, Ohwashi, Tukuba, Ibaraki 305, Japan) and 10 $\mu$g of the transfer plasmid pBm4-TP055 were dissolved in 240 $\mu$l of sterile purified water, and to the solution was added the same volume of 0.5M $CaCl_2$ and 0.1M HEPES, and the mixture was mixed and allowed to stand at a room temperature for 10 minutes. To the mixture was added 480 $\mu$l of 0.2M NaCl, 0.05M HEPES, 0.75 mM $NaH_2PO_4$ and 0.75 mM $Na_2HPO_4$, and the mixture was stirred for a few second and allowed to stand at a room temperature for 20 to 30 minutes to form calcium phosphate gel containing the genomic DNA and the plasmid.

Next, 960 $\mu$l of calcium phosphate gel suspension containing the viral genomic DNA and the transfer vector was added to 4 ml of BoMo15AIIc cells in a 25 $cm^2$ T flask (T25, Corning), and the mixture was allowed to stand for 12 hours. The medium was replaced with a fresh MGM448 (containing 10% FBS and the antibiotics), and culturing was carried out for 25° C. On the sixth day the cultured medium was recovered as a viral solution.

The cultured medium was centrifuged to obtain a clear supernatant, which was then diluted, and added to BoMo15AIIc cells cultured on the microtiter plate, and after 8 days a culturing medium in which viral infection was microscopically observed but a polyhedral body was not formed, was selected (by a limited dilution method). The cultured medium was recovered. Contamination with a wild virus in the viral solution factor was not observed.

A recombinant virus thus constructed, containing a DNA coding for megakaryocyte differentiation factor was designated as TPO55-BmNPV.

(3) Test for expression of recombinant gene

About 1×10$^6$ BoMo15A IIc cells were cultured in 4 ml of MGM448 medium containing 10% FBS on the bottom of 25 $cm^2$ area of a flask for 2 days by plate culture. To the culture, 0.5 moi of wild type virus B6E or recombinant virus (TPO55-BmNPV) containing a gene coding for megakaryocyte differentiation factor were added and BoMo15A IIC cells infected, and the cells were cultured at 25° C. for 3 days, and total RNA was extracted using Isogen (Wako Pure Chemical). Similarly, total RNA was extracted from non-infected BoMo 15AIIc cells.

Next, 1 Mg of the RNA thus extracted was size-fractionated by agarose gel electrophoresis, and the separated RNA was transferred to a Zetaprobe membrane by the capillary action. The membrane was soaked in a hybridization buffer containing megakaryocyte differentiation factor cDNA (:PCR product amplified with KY100 and NIO65 described in Example 2.1) (TPO55 probe DNA) labeled with digoxigenin (Boehringer Mannheim), and the mixture was incubated at 42° C. for 12 hours to allow the formation of specific complex of recombinant megakaryocyte differentiation factor mRNA and the TPO55 probe DNA thereof. The complex was then reacted with an alkaline phosphatase-conjugated anti-digoxigenin antibody (Boehringer Mannheim), and the complexed megakaryocyte differentiation factor mRNA was detected by chemoluminescence generated by hydrolysis of Lumigen PPD (AMPPD) (Boehringer Mannheim) according to manufacture's instructions with alkaline phosphates.

Figure 11:
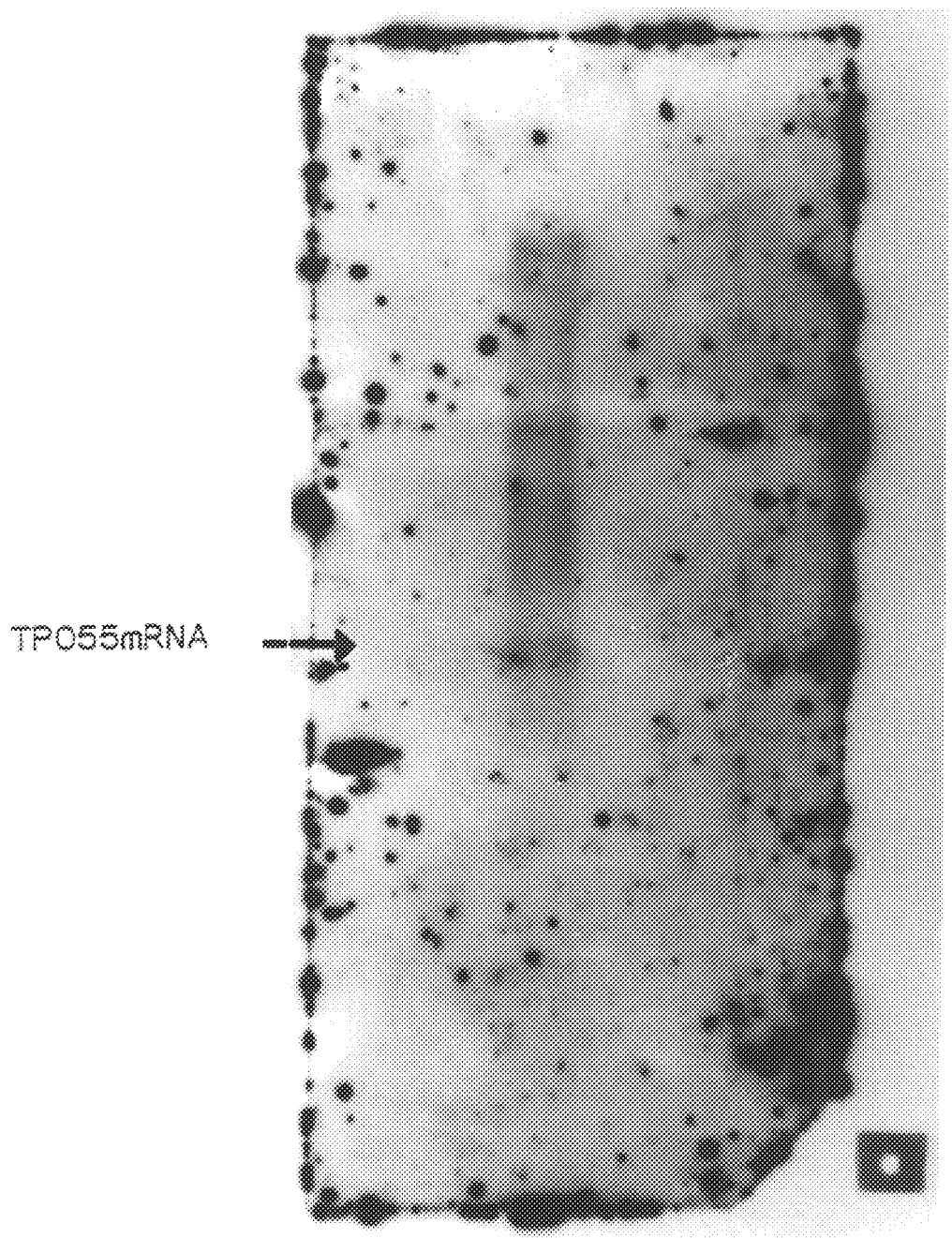
FIG. 11 shows detection of RNA with a DNA probe (PCR product amplified with KY100 and N1065 described in Example 2.1) wherein the RNA was extracted from cultured *Bombyx moli* cells infected with recombinant virus (TP055-Bm NPV) comprising a gene coding for megakaryocyte differentiation factor (Lane B), cells infected with wild type virus (B6E) (Lane A) or from non-transformed cells (Lane C).

As seen in FIG. 11, recombinant megakaryocyte differentiation factor mRNA was detected in total RNA extracted from TPO55-BmNPV-infected cells, and it was shown that the MRNA was expressed in the TP055-BmNPV-infected cells. On the other hand expression of mRNA which hydridized with the probe DNA was not observed in the B6E-infected cells and un-infected cells.

(4) Preparation of solution of recombinant virus

About $1 \times 10^6$ BoMo15AIIc cells were cultured in 4 ml of MGM448 containing 10% FBS on the bottom of a 25 cm$^2$ flask for 2 days, and to this culture was added 10 µl of the culture medium of BoMo15AIIc cells containing the recombinant virus cloned in the above section (2). After culturing at 25° C. for 14 days, the culture medium was centrifuged at 1000 rpm for 5 minutes to obtain a supernatant as a recombinant virus solution.

(5) Preparation of hemolymph of *Bombyx mori*

50 µl/head of a viral solution of the $10^{-1}$-diluted recombinant virus solution obtained in the above section (3) or a $10^{-1}$-diluted wild type virus B6E solution was injected to *Bombyx mori* larvae at 5th instar, and the silkworms were fed with commercially available artificial feed (Morus; Katakura Kogyo) at 20° C. for 4 to 5 days. The abdomens of 50 silkworms were cut, and an extract containing the hemolymph and the content in the central intestine was taken in a plastic tube cooled with ice, and centrifuged to obtain a supernatant.

(6) Confirmation of activity of megakaryocyte differentiation factor 50 ml of the hemolymph of the silkworms obtained in the above section (5) was thoroughly dialyzed against a 20 mM Tris/HCl (pH 7.4) buffer, and applied to a Matrex Blue A column (ϕ2.5×15 cm) equilibrated with the same buffer. The column was thoroughly washed with the same buffer to eliminate an unbound fraction, and a bound protein was eluted by a concentration gradient of 0 to 1M NaCl. An elution profile for megakaryocyte differentiation activity of the hemolymph obtained from silkworms injected with the recombinant virus was compared with that for a wild type virus.

Figure 12:
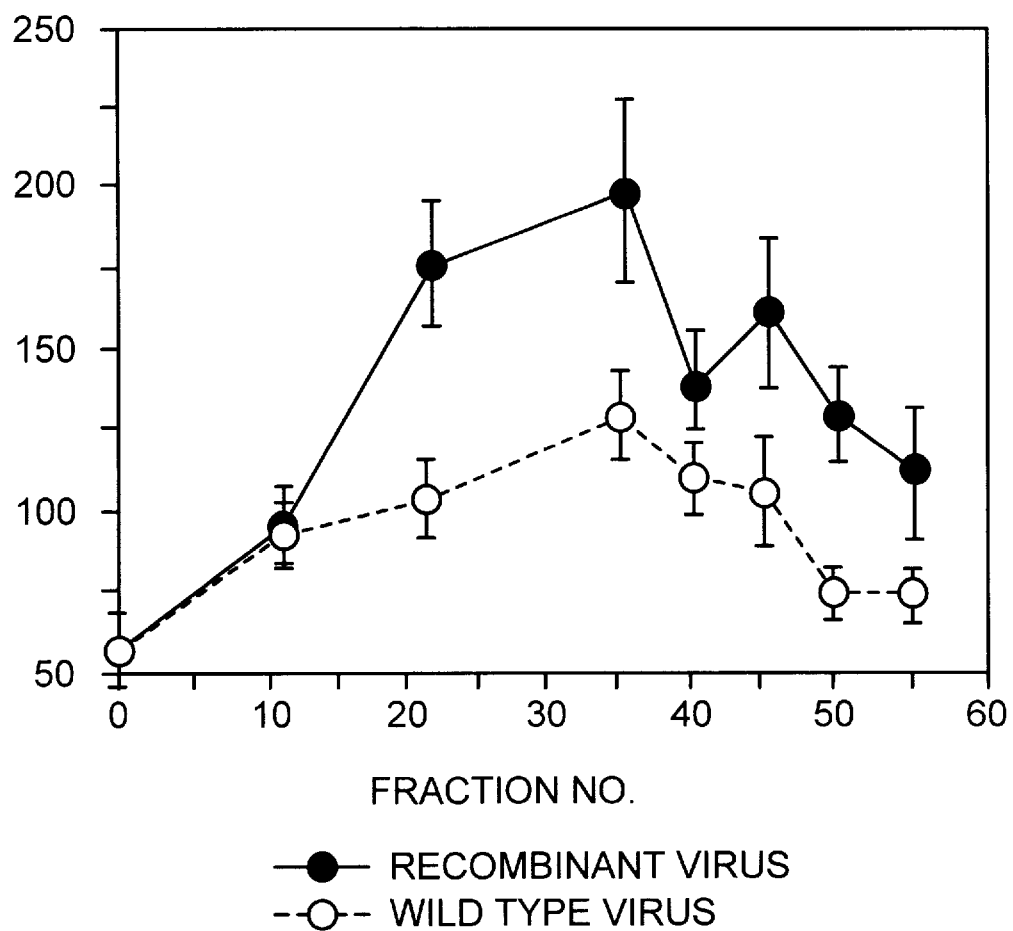
FIG. 12 is a graph showing an expression of megakaryocyte differentiation factor (TP55) in hemolymph of *Bombyx mori* after separation by Matrex Blue A column chromatography.

As seen from FIG. 12, megakaryocyte differentiation activity in the hemolymph from silkworms injected with the recombinant virus was significantly higher than that for the wild type virus.

Although *Bombyx mori* bacurovirus transfer vector pBm4, *Bombyx mori* nuclear polyhedrosis virus PbE and *Bombyx mori* cells BoMo15AIIc were used in Example 4, the present invention is not limited to the use of these materials. Namely, other baculovirus transfer vector (such as pBK283, pBKblue, available from Funakoshi) *Bombyx mori* nuclear polyhedrosis virus (such as purified DNA available from Funakoshi), *Bombyx mori* cells (such as BmN4 cells, available from Funakoshi) can be easily used by a person with ordinary skill in the art to obtain a megakaryocyte differentiation factor.

A megakaryocyte differentiation factor of the present invention accelerates formation of megakaryocytes from myeloid cells in the presence of IL-3. The present megakaryocyte differentiation factor plays an important role in differentiation of megakaryocytes and acts in vivo as a thrombopoietin. Accordingly, the present megakaryocyte differentiation factor may be medicaments effective to not only various diseases involving decrease of platelets but also for control of the number of platelets decreasing by radiation in the case of bone marrow transradiation, or for control of the number of platelets in chemotherapy of cancers.

We claim:

1. An isolated DNA coding for a megakaryocyte differentiation factor having the following properties:
   (1) stimulating differentiation of megakaryocytes
   (2) exhibiting a molecular weight of 55 to 57 kD as determined by gel filtration and SDS-polyacrylamide gel electrophoresis (SDS-PAGE), and having no intermolecular disulfide linkage;
   (3) exhibiting an isoelectric point of 6.5±0.5; and
   (4) having at least one of the amino acid sequences shown in SEQ ID NO: 1 to 9.

2. An isolated DNA coding for a megakaryocyte differentiation factor which stimulates differentiation of megakaryocytes and wherein the amino acid sequence is selected from the group consisting of:
   the amino acid sequence shown in SEQ ID NO: 34;
   a modified amino acid sequence wherein 1 to 30 amino acid residues of the amino acid sequence shown in SEQ ID NO: 34 are deleted;
   a modified amino acid sequence wherein 1 to 10 amino acid residues of the amino acid sequence shown in SEQ ID NO: 34 are replaced with other amino acids;
   a modified amino acid sequence wherein at least one amino acid residue is added to the amino acid sequence shown in SEQ ID NO: 34; and
   an amino acid sequence including a combination of said modifications of the amino acid sequences.

3. An expression vector comprising a DNA according to claim 1.

4. An expression vector comprising a DNA according to claim 2.

5. An isolated eukaryotic or prokaryotic host cell transformed with an expression vector according to claim 3.

6. An isolated eukaryotic or prokaryotic host cell transformed with an expression vector according to claim 4.

7. A process for production of a megakaryocyte differentiation factor having the following properties:
   (1) stimulating differentiation of megakaryocytes;
   (2) exhibiting a molecular weight of 55 to 57 kD as determined by gel filtration and SDS-polyacrylamide gel electrophoresis (SDS-PAGE), and having no intermolecular disulfide linkage;
   (3) exhibiting an isoelectric point of 6.5±0.5; and
   (4) having at least one of the amino acid sequences shown in SEQ ID NO: 1 to 9
comprising the steps of culturing an isolated eukaryotic or prokaryotic host cell transformed with an expression vector, comprising a DNA encoding said megakaryocyte differentiation factor under conditions suitable for producing the megakaryocyte differentiation factor, and recovering the megakaryocyte differentiation factor.

8. A process according to claim 7, wherein the host cell is of silkworm *Bombyx mori.*

9. A process for production of a megakaryocyte differentiation factor which stimulates differentiation of megakaryocytes and wherein the amino acid sequence is selected from the group consisting of:
   the amino acid sequence shown in SEQ ID NO: 34;
   a modified amino acid sequence wherein 1 to 30 amino acid residues of the amino acid sequence shown in SEQ ID NO: 34 are deleted;
   a modified amino acid sequence wherein 1 to 10 amino acid residues of the amino acid sequence shown in SEQ ID NO: 34 are replaced with other amino acids;
   a modified amino acid sequence wherein at least one amino acid sequence is added to the amino acid sequence shown in SEQ ID NO: 34; and
   an amino acid sequence including a combination of said modifications of the amino acid sequences,
comprising the steps of culturing an isolated eukaryotic or prokaryotic host cell transformed with an expression vector comprising a DNA encoding said megakaryocyte differentiation factor under conditions suitable for producing the megakaryocyte differentiation factor, and recovering the megakaryocyte differentiation factor.

10. A process according to claim 9, wherein the host cell is of silkworm *Bombyx mori.*

* * * * *

UNITED STATES PATENT AND TRADEMARK OFFICE
CERTIFICATE OF CORRECTION

PATENT NO. : 5,874,253
DATED : February 23, 1999
INVENTOR(S) : Tsujimoto, et. al.

It is certified that error appears in the above-identified patent and that said Letters Patent is hereby corrected as shown below:

Column 42, line 37 (claim 9) delete "sequence" and insert therefor--residue--.

Signed and Sealed this

Seventh Day of March, 2000

Attest:

Q. TODD DICKINSON

*Attesting Officer*   *Commissioner of Patents and Trademarks*

UNITED STATES PATENT AND TRADEMARK OFFICE
CERTIFICATE OF CORRECTION

PATENT NO. : 5,874,253
DATED : February 23, 1999
INVENTOR(S) : Tsujimoto, et. al.

It is certified that error appears in the above-identified patent and that said Letters Patent is hereby corrected as shown below:

Title page, following paragraph [62], insert the following: item [30], under Foreign Application Priority
Data – July 17, 1992   [JP]   Japan.....................................4-212305
         March 4, 1993   [JP]   Japan.....................................5-067339

Signed and Sealed this

Eleventh Day of July, 2000

*Attest:*

Q. TODD DICKINSON

*Attesting Officer*          *Director of Patents and Trademarks*